(12) United States Patent
Tso et al.

(10) Patent No.: US 7,888,485 B2
(45) Date of Patent: Feb. 15, 2011

(54) ANTI-PLEIOTROPHIN ANTIBODIES AND METHODS OF USE THEREOF

(75) Inventors: J. Yun Tso, Menlo Park, CA (US); Anton Wellstein, Washington, DC (US); Debra Chao, Fremont, CA (US)

(73) Assignee: Georgetown University, Washington, DC (US)

( * ) Notice: Subject to any disclaimer, the term of this patent is extended or adjusted under 35 U.S.C. 154(b) by 1083 days.

(21) Appl. No.: 10/812,366

(22) Filed: Mar. 26, 2004

(65) Prior Publication Data

US 2004/0234519 A1 Nov. 25, 2004

Related U.S. Application Data

(60) Provisional application No. 60/458,459, filed on Mar. 26, 2003.

(51) Int. Cl.
A61K 39/395 (2006.01)
C07K 16/22 (2006.01)
C07K 16/30 (2006.01)
C12N 5/20 (2006.01)
C12P 21/08 (2006.01)

(52) U.S. Cl. .............................. 530/388.24; 424/141.1; 424/145.1; 424/155.1; 424/158.1; 424/174.1; 435/70.21; 435/452; 435/336; 435/344; 435/344.1; 436/548; 530/387.3; 530/388.8; 530/388.85; 530/389.2; 530/389.7; 530/391.7

(58) Field of Classification Search .............. 435/70.21, 435/452, 336, 344, 344.1; 436/548; 530/387.3, 530/388.24, 388.8, 388.85, 389.2, 389.7, 530/391.7; 424/141.1, 145.1, 155.1, 158.1, 424/174.1

See application file for complete search history.

(56) References Cited

U.S. PATENT DOCUMENTS

| 5,675,063 | A * | 10/1997 | Knight | .......................... 800/14 |
|---|---|---|---|---|
| 5,770,421 | A | 6/1998 | Morris et al. | |
| 6,562,346 | B1 * | 5/2003 | Paliard et al. | ............ 424/189.1 |
| 6,569,431 | B2 * | 5/2003 | von Budingen et al. | .. 424/142.1 |
| 2002/0034768 | A1 | 3/2002 | Wellstein | |
| 2002/0173629 | A1* | 11/2002 | Jakobovits et al. | ..... 530/388.22 |
| 2003/0073623 | A1 | 4/2003 | Drmanac et al. | |
| 2003/0158132 | A1 | 8/2003 | Kovesdi | |
| 2003/0202960 | A1 | 10/2003 | Colley | |

FOREIGN PATENT DOCUMENTS

| EP | 89101187.6 | 9/1993 |
|---|---|---|
| EP | 91870003.0 | 5/1997 |
| WO | WO0020869 A1 | 4/2000 |
| WO | WO0196394 A2 | 12/2001 |

OTHER PUBLICATIONS

Rudikoff et al., 1982. Single amino acid substitution altering antigen-binding specificity. Proc. Natl. Acad. Sci. USA 79: 1979-1983.*
Roes et al., 1995. Mouse anti-mouse IgD monoclonal antibodies generated in IgD-deficient mice. J. Immunological Methods 183: 231-237.*
Harlow et al., 1988. Antibodies. A Laboratory Manual, Cold Spring Harbor Laboratory, Cold Spring Harbor. pp. 72-77.*
Rauvala, 1989. An 18-kd heparin-binding protein of developing brain that is distinct from fibroblast growth factors. The EMBO Journal 10: 2933-2941.*
Ledoux et al., 1997. Cellular distribution of the angiogenic factor heparin affin regulatory peptide (HARP) mRNA and protein in the human mammary gland. Journal of Histochemistry & Cytochemistry 45: 1239-1245.*
Dreyfus et al., 1998. HB-GAM/Pleiotrophin: localization of mRNA and protein in the chicken developing leg. Int. J. Dev. Biol. 42: 189-198.*
Papadimitriou et al., 2001. HARP induces angiogenesis in vivo and in vitro: implication of N or C terminal peptides. Biochemical and Biophysical Research Communications 282: 306-313.*
Aigner, et al., "Delivery of Unmodified Bioactive Ribozymes by an RNA-Stabilizing Polyethylenimine (LMV-PEI) Efficiently Down-Regulates Gene Expression", *Gene Therapy*, 9:1700-1707 (2002).
Amet, et al., "Enhanced Hippocampal Long-Term Potentiation in Mice Lacking Heparin-Binding Growth-Associated Molecule", *Mol. Cell. Neuro.*, 17:1014-1024 (2001).
Chauhan, et al., "Pleiotrophin Transforms NIH 3T3 Cells and Induces Tumors in Nude Mice", *Proc. Natl. Aacd. Sci. USA*, 90:679-682 (1993).
Choudhuri, et al., "An Angiogenic Role for the Neurokines Midkine and Pleiotrophin in Tumorigenesis", *Can. Res.* 57:1814-1819 (1997).
Czubayko, et al., "Ribozyme-Targeting Elucidates a Direct Role of Pleiotrophin in Tumor Growth", *J. Bio. Chem.*, 269(33):21358-21363, (1994).
Czubayko, et al., "Melanoma Angiogenesis and Metastasis Modulated by Ribozyme Targeting of the Secreted Growth Factor Pleiotrophin", *Proc. Natl. Aacd. Sci.*, 93:14753-14758 (1996).
Fang, et al., "Pleiotrophin Stimulates Fibroblasts and Endothelial and Epithelial Cells and is Expressed in Human Cancer", *J. Bio Chem.*, 267(36):25889-25897 (1992).
Jager, et al., "Differential Expression and Biological Activity of the Heparin-Binding Growth-Associated Molecule (HB-GAM) in Lung Cancer Cell Lines", *Int. J. Cancer*, 73:537-543 (1997).
Jager, et al.,"Serum Levels of the Angiogenic Factor Pleiotrophin in Relation to Disease Stage in Lung Cancer Patients", *British J of Cancer*, 86:858-863 (2002).

(Continued)

*Primary Examiner*—Shafiqul Haq
*Assistant Examiner*—James L Grun
(74) *Attorney, Agent, or Firm*—Ropes & Gray LLP

(57) ABSTRACT

The present invention concerns antibodies that neutralize at least one biological activity of pleiotrophin. The antibodies can inhibit cancer cell growth and angiogenesis in vitro or in vivo. The present invention provides for methods of inhibiting cancer cell growth or angiogenesis in a subject comprising administering to said subject an effective amount of the antibodies described herein. The present invention also provides for methods of making the neutralizing antibodies described herein.

8 Claims, 14 Drawing Sheets

OTHER PUBLICATIONS

Klomp, et al., "Significance of the Expression of the Growth Factor Pleiotrophin in Pancreatic Cancer Patients", *Clinical Cancer Res.*, 8:823-827 (2002).

Muramatsu, "Midkine and Pleiotrophin: Two Related Proteins Involved in Development, Survival, Inflammation and Tumorigenesis", *J. Bio. Chem.*, 132:359-371 (2002).

Nakagawara, et al., "Differential Expression of Pleiotrophin and Midkine in Advanced Neuroblastomas", *Can. Res.*, 55:1792-1797 (1995).

Schulte, et al., "Human Trophoblast and Choriocarcinoma Expression of the Growth Factor Pleiotrophin Attributable to Germ-Line Insertion of an Endogenous Retrovirus", *Proc. Natl. Aacd. Sci. USA*, 93:14579-14764 (1996).

Sette, et al., "Structural Characteristics of an Antigen Required for its Interaction with Ia and Recognition by T Cells", *Nature*, 328:395-399 (1987).

Seykora, et al., "Gene Expression Profiling of Melanocytic Lesions", *Am. J. of Dermatopathology.*, 25(1):6-11 (2003).

Vacherot, et al., "Involvement of Heparin Affin Regulatory Peptide in Human Prostate Cancer", *The Prostate*, 38:126-136 (1999).

Weber, et al., "Pleiotrophin Can be Rate-Limiting for Pancreatic Cancer Cell Growth", *Can. Res.*, 60:5284-5288 (2000).

Wellstein, et al., "A Heparin-Binding Growth Factor Secreted from Breast Cancer Cells Homologous to a Developmentally Regulated Cytokine", *J. Biol. Chem.*, 267(4):2582-2587 (1992).

* cited by examiner

Top line = human pleiotrophin (SEQ ID NO:1)
Bottom line = mouse pleiotrophin (SEQ ID NO:2)

```
          10        20        30        40        50        60
MQAQQYQQQRRKFAAAFLAFIFILAAVDTAEAGKKEKPEKKVKKSDCGEWQWSVCVPTSG
MSSQQYQQQRRKFAAAFLALIFILAAVDTAEAGKKEKPEKKVKKSDCGEWQWSVCVPTSG 90       100       110       120       130       140
DCGLGTREGTRTGAECKQTMKTQRCKIPCNWKKQFGAECKYQFQAWGECDLNTALKTRTG
DCGLGTREGTRTGAECKQTMKTQRCKIPCNWKKQFGAECKYQFQAWGECDLNTALKTRTG 150       160       170       180
SLKRALHNAECQKTVTISKPCGKLTKPKPQAESKKKKKEGKKQEKMLD
SLKRALHNADCQKTVTISKPCGKLTKPKPQAESKKKKKEGKKQEKMLD
```

FIG. 1A

Amino acid sequence (SEQ ID NO:3) and the nucleotide sequence (SEQ ID NO:4) of the heavy chain variable region (VH) of 3B10.

```
CAGGTTCAGCTGCAGCAGTCTGGACCTGAGCTGGTGAAGCCTGGGGCCTCAGTGAAGATT
 Q   V   Q   L   Q   Q   S   G   P   E   L   V   K   P   G   A   S   V   K   I

TCCTGCCAAGCTTCTGGCTACGCATTCAGTAGCCACTGGATGAACTGGGTGAAGCAGAGG
 S   C   Q   A   S   G   Y   A   F   S   S   H   W   M   N   W   V   K   Q   R

CCTGGAAAGGGTCTTGAGTGGATTGGACGGATTTATCCTGGAGATGGAGATTCTCTCTAC
 P   G   K   G   L   E   W   I   G   R   I   Y   P   G   D   G   D   S   L   Y

AATGGGAAGTTCAAGGGCAAGGCCACACTGACTGCAGACAAATCCTCCACCACAGTCTAC
 N   G   K   F   K   G   K   A   T   L   T   A   D   K   S   S   T   T   V   Y

ATGCAGCTCAGCAGCCTGACATCTGAGGACTCTGCGGTCTACTTCTGTGCAAGAACGAGG
 M   Q   L   S   S   L   T   S   E   D   S   A   V   Y   F   C   A   R   T   R

GCTTATGGTCCCGCCTGGTTTGCTTACTGGGGCCAAGGGACTCTGGTCACTGTCTCT
 A   Y   G   P   A   W   F   A   Y   W   G   Q   G   T   L   V   T   V   S

GCA
 A
```

FIG. 1B

Amino acid sequence (SEQ ID NO:8) and the nucleotide sequence (SEQ ID NO:9) of the light chain variable region (VL) of 3B10.

```
GACATTGTGATGACACAGTCTCCATCCTCCCTGGCTATGTCAGTAGGACAGAAG
 D   I   V   M   T   Q   S   P   S   S   L   A   M   S   V   G   Q   K

GTCACTTTGAGCTGCAGGTCCAGTCAGAGTCTTTTAGATAGTAACAATCAAAAGAAC
 V   T   L   S   C   R   S   S   Q   S   L   L   D   S   N   N   Q   K   N

TATTTGGCCTGGTACCAGCAGAAACCGGGACAGTCTCCTAAACTTCTGGTATACYTT
 Y   L   A   W   Y   Q   Q   K   P   G   Q   S   P   K   L   L   V   Y   -

GCATCTATTAGGGAATCTGGGGTCCCTGATCGCTTCATAGGCAGTGGATCTGGGACA
 A   S   I   R   E   S   G   V   P   D   R   F   I   G   S   G   S   G   T

GATTTCACTCTTACCATCACCAGTGTGCAGGCTGAAGACCTGGCAGATTATTTCTGT
 D   F   T   L   T   I   T   S   V   Q   A   E   D   L   A   D   Y   F   C

CAGCAACATTATAGCACTCCCCTCACGTTCGGTGCTGGGACCAAGCTGGAGCTGAAA
 Q   Q   H   Y   S   T   P   L   T   F   G   A   G   T   K   L   E   L   K
```

FIG. 1C

Amino acid sequence of the murine PTN-Fc fusion protein (SEQ ID NO:13)

Amino acid sequence of PTN-OVA fusion protein (SEQ ID NO:14). OVA insertion sequence (SEQ ID NO:15) is underlined.

(A)
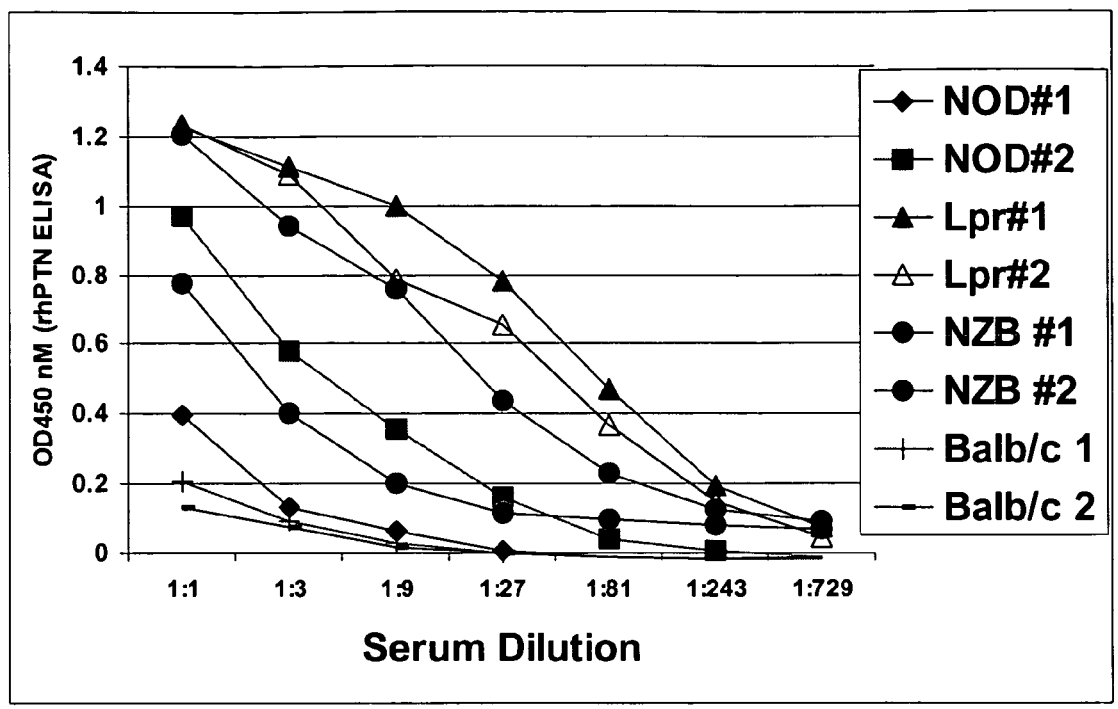
(B)
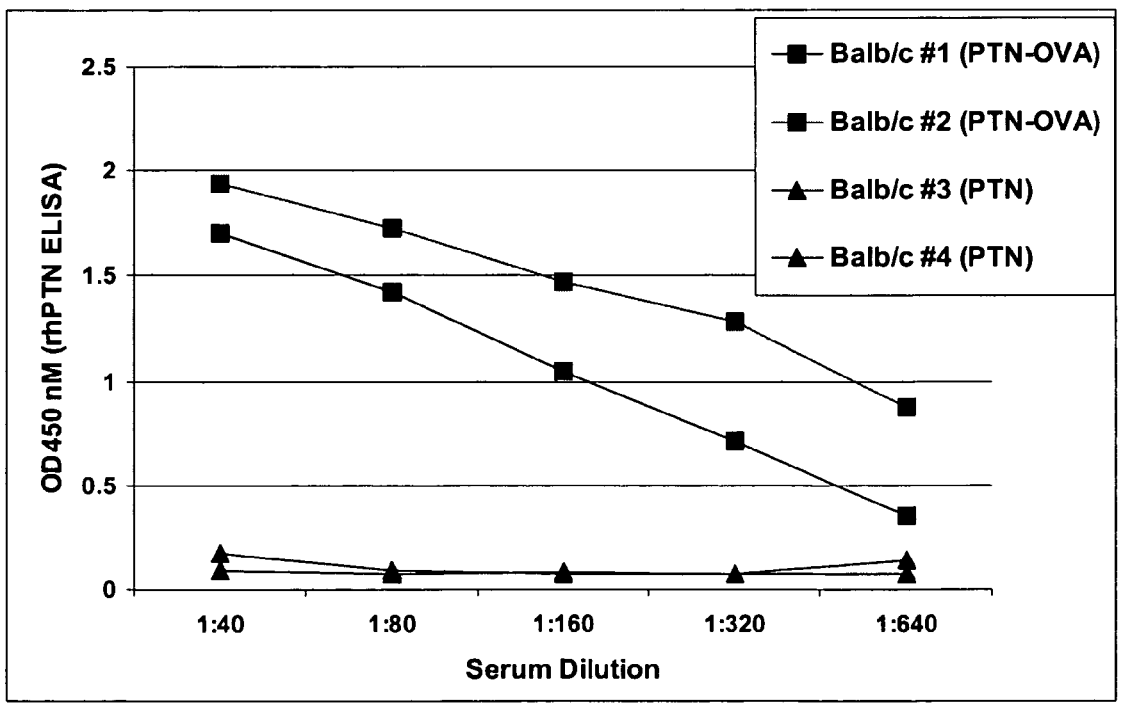
FIG. 6

SW13/PTN C.M 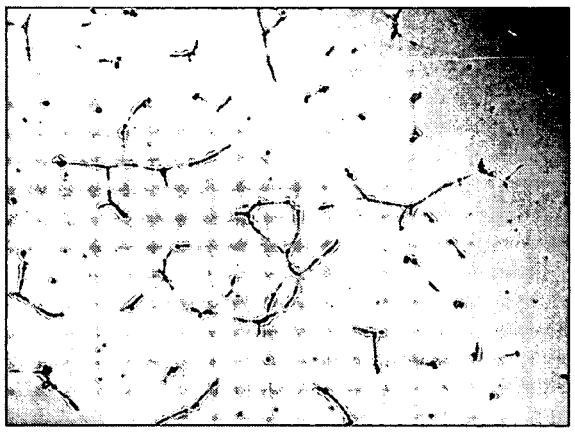  SW13/PTN C.M + #27 (5 µg/ml). 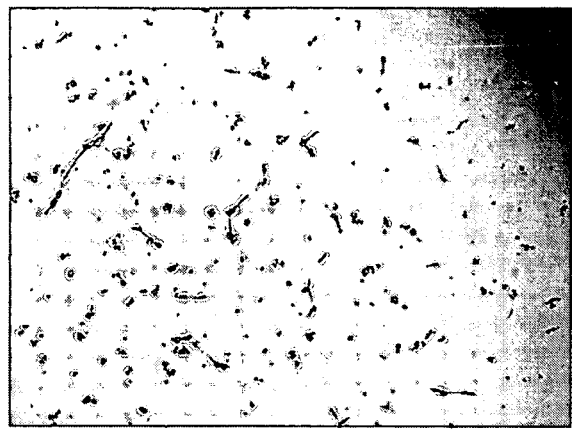
FIG. 10

SEQUENCE LISTING

<160> NUMBER OF SEQ ID NOS: 15

<210> SEQ ID NO 1
<211> LENGTH: 168
<212> TYPE: PRT
<213> ORGANISM: Homo Sapiens

<400> SEQUENCE: 1

Met Gln Ala Gln Gln Tyr Gln Gln Arg Arg Lys Phe Ala Ala Ala
1               5                   10                  15

Phe Leu Ala Phe Ile Phe Ile Leu Ala Ala Val Asp Thr Ala Glu Ala
                20                  25                  30

Gly Lys Lys Glu Lys Pro Glu Lys Val Lys Ser Asp Cys Gly
                35                  40                  45

Glu Trp Gln Trp Ser Val Cys Val Pro Thr Ser Gly Asp Cys Gly Leu
50                      55                      60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
                100                 105                 110

Thr Ala Leu Lys Thr Arg Thr Gly Ser Leu Lys Arg Ala Leu His Asn
                115                 120                 125

Ala Glu Cys Gln Lys Thr Val Thr Ile Ser Lys Pro Cys Gly Lys Leu
                130                 135                 140

Thr Lys Pro Lys Pro Gln Ala Glu Ser Lys Lys Lys Lys Glu Gly
145                 150                 155                 160

Lys Lys Gln Glu Lys Met Leu Asp
                165

<210> SEQ ID NO 2
<211> LENGTH: 168
<212> TYPE: PRT
<213> ORGANISM: Mus Musculus

<400> SEQUENCE: 2

Met Ser Ser Gln Gln Tyr Gln Gln Arg Arg Lys Phe Ala Ala Ala
1               5                   10                  15

Phe Leu Ala Leu Ile Phe Ile Leu Ala Ala Val Asp Thr Ala Glu Ala
                20                  25                  30

Gly Lys Lys Glu Lys Pro Glu Lys Val Lys Ser Asp Cys Gly
                35                  40                  45

Glu Trp Gln Trp Ser Val Cys Val Pro Thr Ser Gly Asp Cys Gly Leu
50                      55                      60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
                100                 105                 110

Thr Ala Leu Lys Thr Arg Thr Gly Ser Leu Lys Arg Ala Leu His Asn
                115                 120                 125

Ala Asp Cys Gln Lys Thr Val Thr Ile Ser Lys Pro Cys Gly Lys Leu
                130                 135                 140

```
Thr Lys Pro Lys Pro Gln Ala Glu Ser Lys Lys Lys Lys Glu Gly
145                 150                 155                 160

Lys Lys Gln Glu Lys Met Leu Asp
                165
```

<210> SEQ ID NO 3
<211> LENGTH: 120
<212> TYPE: PRT
<213> ORGANISM: Homo Sapiens

<400> SEQUENCE: 3

```
Gln Val Gln Leu Gln Gln Ser Gly Pro Glu Leu Val Lys Pro Gly Ala
1               5                   10                  15

Ser Val Lys Ile Ser Cys Gln Ala Ser Gly Tyr Ala Phe Ser Ser His
            20                  25                  30

Trp Met Asn Trp Val Lys Gln Arg Pro Gly Lys Gly Leu Glu Trp Ile
        35                  40                  45

Gly Arg Ile Tyr Pro Gly Asp Gly Asp Ser Leu Tyr Asn Gly Lys Phe
    50                  55                  60

Lys Gly Lys Ala Thr Leu Thr Ala Asp Lys Ser Ser Thr Thr Val Tyr
65                  70                  75                  80

Met Gln Leu Ser Ser Leu Thr Ser Glu Asp Ser Ala Val Tyr Phe Cys
                85                  90                  95

Ala Arg Thr Arg Ala Tyr Gly Pro Ala Trp Phe Ala Tyr Trp Gly Gln
            100                 105                 110

Gly Thr Leu Val Thr Val Ser Ala
        115                 120
```

<210> SEQ ID NO 4
<211> LENGTH: 360
<212> TYPE: DNA
<213> ORGANISM: Homo Sapiens

<400> SEQUENCE: 4

```
caggttcagc tgcagcagtc tggacctgag ctggtgaagc ctggggcctc agtgaagatt      60
tcctgccaag cttctggcta cgcattcagt agccactgga tgaactgggt gaagcagagg     120
cctggaaagg gtcttgagtg gattggacgg atttatcctg gagatggaga ttctctctac     180
aatgggaagt tcaagggcaa ggccacactg actgcagaca atcctccaca cagtctac      240 atgcagctca gcagcctgac atctgaggac tctgcggtct acttctgtgc aagaacgagg     300
gcttatggtc ccgcctggtt tgcttactgg ggccaaggga ctctggtcac tgtctctgca     360
```

<210> SEQ ID NO 5
<211> LENGTH: 5
<212> TYPE: PRT
<213> ORGANISM: Homo Sapiens

<400> SEQUENCE: 5

```
Ser His Trp Met Asn
1               5
```

<210> SEQ ID NO 6
<211> LENGTH: 17
<212> TYPE: PRT
<213> ORGANISM: Homo Sapiens

<400> SEQUENCE: 6

```
Arg Ile Tyr Pro Gly Asp Gly Asp Ser Leu Tyr Asn Gly Lys Phe Lys
```

```
1               5                   10                  15
Gly

<210> SEQ ID NO 7
<211> LENGTH: 11
<212> TYPE: PRT
<213> ORGANISM: Homo Sapiens

<400> SEQUENCE: 7

Thr Arg Ala Tyr Gly Pro Ala Trp Phe Ala Tyr
1               5                   10

<210> SEQ ID NO 8
<211> LENGTH: 112
<212> TYPE: PRT
<213> ORGANISM: Homo Sapiens

<400> SEQUENCE: 8

Asp Ile Val Met Thr Gln Ser Pro Ser Ser Leu Ala Met Ser Val Gly
1               5                   10                  15

Gln Lys Val Thr Leu Ser Cys Arg Ser Ser Gln Ser Leu Leu Asp Ser
            20                  25                  30

Asn Asn Gln Lys Asn Tyr Leu Ala Trp Tyr Gln Gln Lys Pro Gly Gln
        35                  40                  45

Ser Pro Lys Leu Leu Val Tyr Ala Ser Ile Arg Glu Ser Gly Val Pro
    50                  55                  60

Asp Arg Phe Ile Gly Ser Gly Ser Gly Thr Asp Phe Thr Leu Thr Ile
65                  70                  75                  80

Thr Ser Val Gln Ala Glu Asp Leu Ala Asp Tyr Phe Cys Gln Gln His
                85                  90                  95

Tyr Ser Thr Pro Leu Thr Phe Gly Ala Gly Thr Lys Leu Glu Leu Lys
            100                 105                 110

<210> SEQ ID NO 9
<211> LENGTH: 339
<212> TYPE: DNA
<213> ORGANISM: Homo Sapiens

<400> SEQUENCE: 9
gacattgtga tgacacagtc tccatcctcc ctggctatgt cagtaggaca gaaggtcact      60
ttgagctgca ggtccagtca gagtctttta gatagtaaca atcaaaagaa ctatttggcc    120
tggtaccagc agaaaccggg acagtctcct aaacttctgg tatacyttgc atctattagg    180
gaatctgggg tccctgatcg cttcataggc agtggatctg gacagatttt cactcttacc    240
atcaccagtg tgcaggctga agacctggca gattatttct gtcagcaaca ttatagcact    300
cccctcacgt tcggtgctgg gaccaagctg gagctgaaa                          339

<210> SEQ ID NO 10
<211> LENGTH: 17
<212> TYPE: PRT
<213> ORGANISM: Homo Sapiens

<400> SEQUENCE: 10

Arg Ser Ser Gln Ser Leu Leu Asp Ser Asn Asn Gln Lys Asn Tyr Leu
1               5                   10                  15

Ala

<210> SEQ ID NO 11
```

```
<211> LENGTH: 6
<212> TYPE: PRT
<213> ORGANISM: Homo Sapiens

<400> SEQUENCE: 11

Ala Ser Ile Arg Glu Ser
1               5

<210> SEQ ID NO 12
<211> LENGTH: 9
<212> TYPE: PRT
<213> ORGANISM: Homo Sapiens

<400> SEQUENCE: 12

Gln Gln His Tyr Ser Thr Pro Leu Thr
1               5

<210> SEQ ID NO 13
<211> LENGTH: 387
<212> TYPE: PRT
<213> ORGANISM: Mus Musculus

<400> SEQUENCE: 13

Met Gly Trp Ser Trp Ile Phe Leu Phe Leu Leu Ser Gly Thr Ala Ser
1               5                   10                  15

Val His Ser Gly Lys Lys Glu Lys Pro Glu Lys Val Lys Lys Ser
            20                  25                  30

Asp Cys Gly Glu Trp Gln Trp Ser Val Cys Val Pro Thr Ser Gly Asp
            35                  40                  45

Cys Gly Leu Gly Thr Arg Glu Gly Thr Arg Thr Gly Ala Glu Cys Lys
        50                  55                  60

Gln Thr Met Lys Thr Gln Arg Cys Lys Ile Pro Cys Asn Trp Lys Lys
65                  70                  75                  80

Gln Phe Gly Ala Glu Cys Lys Tyr Gln Phe Gln Ala Trp Gly Glu Cys
                85                  90                  95

Asp Leu Asn Thr Ala Leu Lys Thr Arg Thr Gly Ser Leu Lys Arg Ala
            100                 105                 110

Leu His Asn Ala Asp Cys Gln Lys Thr Val Thr Ile Ser Lys Pro Cys
        115                 120                 125

Gly Lys Leu Thr Lys Pro Lys Pro Gln Ala Glu Ser Lys Lys Lys Lys
    130                 135                 140

Lys Glu Gly Lys Lys Gln Glu Lys Met Leu Asp Thr Gly Gly Gly Glu
145                 150                 155                 160

Arg Lys Cys Cys Val Glu Cys Pro Cys Pro Ala Pro Pro Ala Ala
                165                 170                 175

Ala Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Gln Phe Asn Trp Tyr Val Asp Gly Val Glu Val
    210                 215                 220

His Asn Ala Lys Thr Lys Pro Arg Glu Glu Gln Phe Asn Ser Thr Phe
225                 230                 235                 240

Arg Val Val Ser Val Leu Thr Val Val His Gln Asp Trp Leu Asn Gly
                245                 250                 255

Lys Glu Tyr Lys Cys Lys Val Ser Asn Lys Gly Leu Pro Ala Pro Ile
            260                 265                 270
```

```
Glu Lys Thr Ile Ser Lys Thr Lys Gly Gln Pro Arg Glu Pro Gln Val
            275                 280                 285

Tyr Thr Leu Pro Pro Ser Arg Glu Glu Met Thr Lys Asn Gln Val Ser
            290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
            325                 330                 335

Met Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
            355                 360                 365

His Glu Ala Leu His Asn His Tyr Thr Gln Lys Ser Leu Ser Leu Ser
            370                 375                 380

Pro Gly Lys
385

<210> SEQ ID NO 14
<211> LENGTH: 174
<212> TYPE: PRT
<213> ORGANISM: Homo Sapiens

<400> SEQUENCE: 14

Met Gln Ala Gln Gln Tyr Gln Gln Gln Arg Arg Lys Phe Ala Ala Ala
1               5                   10                  15

Phe Leu Ala Phe Ile Phe Ile Leu Ala Ala Val Asp Thr Ala Glu Ala
            20                  25                  30

Gly Lys Lys Glu Lys Pro Glu Lys Val Lys Lys Ser Asp Cys Gly
            35                  40                  45

Glu Trp Gln Trp Ser Val Cys Val Pro Thr Ser Gly Asp Cys Gly Leu
50                  55                  60

Gly Thr Arg Glu Gly Thr Arg Thr Gly Ala Glu Cys Lys Gln Thr Met
65                  70                  75                  80

Lys Thr Gln Arg Cys Lys Ile Pro Cys Asn Trp Lys Lys Gln Phe Gly
                85                  90                  95

Ala Glu Cys Lys Tyr Gln Phe Gln Ala Trp Gly Glu Cys Asp Leu Asn
            100                 105                 110

Thr Ala Leu Lys Thr Arg Thr Gly Ser Leu Lys Arg Gln Ala Val His
            115                 120                 125

Ala Ala His Ala Glu Ile Asn Glu Cys Gln Lys Thr Val Thr Ile Ser
            130                 135                 140

Lys Pro Cys Gly Lys Leu Thr Lys Pro Lys Pro Gln Ala Glu Ser Lys
145                 150                 155                 160

Lys Lys Lys Lys Glu Gly Lys Lys Gln Glu Lys Met Leu Asp
                165                 170

<210> SEQ ID NO 15
<211> LENGTH: 11
<212> TYPE: PRT
<213> ORGANISM: Homo Sapiens

<400> SEQUENCE: 15

Gln Ala Val His Ala Ala His Ala Glu Ile Asn
1               5                   10
```

ANTI-PLEIOTROPHIN ANTIBODIES AND METHODS OF USE THEREOF

RELATED APPLICATIONS

This application claims priority from U.S. Provisional Application No. 60/458,459 filed Mar. 26, 2003.

FIELD OF THE INVENTION

This invention relates to the field of immunology and cancer therapy. In particular, it concerns neutralizing anti-pleiotrophin antibodies, the methods of making, and the methods of using thereof for the treatment of cancer.

BACKGROUND OF THE INVENTION

The growth of solid tumors induces and requires a network of growth signals between the tumor cells and the surrounding tissues. The tumor cells often secret growth factors that promotes self-growth (autocrine action) and stimulate angiogenesis (paracrine action), which is the recruitment of blood vessels, to support the tumor growth in vivo (Folkman, et al., Semin. Oncol. 29: 15 (2002)). Ideally, therapeutic agents that block both autocrine and paracrine functions will be more effective in treating cancer patients.

Pleiotrophin (PTN) is a secreted, heparin-binding growth factor that is highly expressed during development but with very specific and limited expression in normal adult tissues (see review by Muramatsu, J. Bio. Chem. 132: 359-371 (2002)). PTN has been shown to stimulate the growth of fibroblasts, endothelial cells, and different tumor epithelial cells in vitro (Fang et al., J. Bio. Chem. 267: 25889-25897 (1992)).

Over-expression of PTN in cells results in malignant phenotypes that include anchorage-independent growth in vitro and tumorigenicity in nude mice (Chauhan et al., Proc. Natl. Aacd. Sci. 90: 679-682, (1993)). PTN also displays angiogenic activity in the rabbit corneal assay when it is expressed in MCF-7 cells (Choudhuri et al., Can. Res. 57: 1814-1819 (1997)). Screening of various human tumor cell lines and tumor specimens has revealed that PTN is expressed in nearly 50% of tumor cell lines of different origin, such as melanoma, neuroblastoma, breast, prostate, lung, and pancreatic cancers (Nakagawara et al., Can. Res. 55: 1792-1797 (1995); Jager et al., Int. J. Cancer 73: 537-534 (1997); Czybayko et al., Proc. Natl. Aacd. Sci. 93: 14753-14758 (1996); Vacherot et al., The Prostate 38: 126-136 (1999); Weber et al., Can. Res. 60: 5284-5288, (2000)). In addition, the PTN level in serum is elevated in pancreatic, lung and colon cancer patients; and it may correlate with disease stages (Jager et al., British J of Cancer 86: 858-863, (2002); Klomp et al., Clinical Cancer Res. 8: 823-827, (2002)). Moreover, depletion of PTN by ribozyme in tumor cells suppresses tumor growth and metastasis in mice including melanoma, (Czubayko et al., J. Bio. Chem. 269: 21358-21363, (1994); Czybayko et al., Proc. Natl. Aacd. Sci. 93: 14753-14758, (1996); Aigner et al., Gene Therapy. 9: 1700-1707 (2002)), choriocarcinoma (Schulte et al., Proc. Natl. Aacd. Sci. 93: 14579-14764 (1996)) and pancreatic cancer (Weber et al., Can. Res. 60: 5284-5288, (2000)).

U.S. Pat. No. 5,770,421 discusses the isolation and cloning of a receptor of PTN, ALK (Anaplastic Lymphoma Kinase), as well as the use of the anti-ALK antibodies for detecting ALK (This and all other U.S. patents and patent applications cited herein are hereby incorporated by reference in their entirety). Ribozyme-mediated reduction of ALK leads to the reduction of tumor size and increase of the animal survival in xenograft model of U87MG cells (WO 0196394A2 and Patent Application U.S. 2002/034768A1). Therapeutic use of antibodies against ALK has not been examined in any of the above-referenced publications.

It is therefore desirable to develop blocking reagents, such as antibodies, that block PTN functions including oncogenic and angiogenic activities.

The development of therapeutic antibodies often begins with raising antibodies in mice against an injected human protein target. It is generally difficult to elicit an adequate immune response against proteins that are highly homologous among the mammalian species because the mouse immune system cannot differentiate between the human version of the protein and its own version of the protein. PTN is nearly identical among mammalian species (see FIG. 1 for human and mouse PTN sequence comparison) and thus it is very difficult to generate antibodies against PTN in rodents, especially the neutralizing anti-PTN antibodies. One example of an anti-PTN monoclonal antibody used for the diagnostic purpose is disclosed in PCT Publication No. WO 0020869A1.

The present invention is directed to novel methods of making antibodies against any target proteins. These methods are particularly useful in producing antibodies against the proteins that are highly homologous among the mammalian species. These methods have given rise to multiple neutralizing anti-PTN monoclonal antibodies, which functionally inhibit or block the angiogenic and oncogenic activities of PTN in vitro and/or in vivo, and are therefore of great therapeutic value. The present invention also provides for effective methods of inhibiting cancer growth and angiogenesis in a subject with antagonists of PTN, preferably neutralizing anti-PTN antibodies.

SUMMARY OF THE INVENTION

The present invention is directed to an antibody that competitively inhibits binding of a PTN polypeptide to an antibody comprising a sequence selected from SEQ ID NOs:3, 5, 6, 7, 8, 10, 11 and 12.

In one preferred embodiment, the present invention is directed to an antibody that binds to PTN and neutralizes at least one biological activity of PTN. Preferably, said antibody inhibits cancer cell growth and/or angiogenesis induced by cancer cells. Preferably, the antibodies are monoclonal antibodies including chimeric antibodies, humanized antibodies, fully human antibodies, or the fragments or conjugates thereof.

The present invention is also directed to a heavy chain variable region of an antibody comprising an amino acid sequence of SEQ ID NO:3 and/or a light chain variable region of an antibody comprising an amino acid sequence of SEQ ID NO:8.

The present invention is also directed to a complementarity determining region comprising an amino acid sequence of SEQ ID NO:5, 6, 7, 10, 11, or 12.

The present invention is also directed to a polypeptide comprising an amino acid sequence of SEQ ID NO:3, 5, 6, 7, 8, 10, 11, or 12.

The present invention is also directed to a pharmaceutical composition comprising antibodies that bind to PTN and neutralize at least one biological activity of PTN.

The present invention is also directed to a method of neutralizing at least one biological activity of PTN in a subject in need thereof comprising administering to said subject an effective amount of an antagonist of PTN, wherein said antagonist is a polypeptide.

The present invention is also directed to a method of inhibiting angiogenesis induced by cancer cells of a subject in need thereof comprising administering to said subject an effective amount of an antagonist of PTN, wherein said antagonist is a polypeptide.

The present invention is also directed to a method of inhibiting growth of cancer cells of a subject comprising administering to said subject an effective amount of an antagonist of PTN, wherein said antagonist is a polypeptide.

The present invention is also directed to a method of producing an isolated antibody comprising 1) selecting a host animal; 2) immunizing said host animal with a fusion protein comprising said protein connected with a T-cell epitope; 3) isolating a lymphoid cell from said host animal; 4) fusing said lymphoid cell to a myeloma cell, so that a hybrid cell is created; 5) cultivating said hybrid cell; and 6) isolating a monoclonal antibody against said protein. Preferably, said protein is a first protein derived from a human and is highly homologous to a second protein derived from a mouse. More preferably, said first protein includes, but is not limited to a human PTN.

BRIEF DESCRIPTION OF THE DRAWINGS

FIG. 1A. Alignment of human (SEQ ID NO:1) and mouse (SEQ ID NO:2) pleiotrophin amino acid sequences. The only difference in human and mouse PTN sequence is underlined.

FIG. 1B. The deduced amino acid sequence (SEQ ID NO:3) and the nucleotide sequence (SEQ ID NO:4) of the heavy chain variable region (VH) of 3B10. The three complementarity determining regions (CDRs) are underlined, and the first NH2-terminal amino acid residue of the matured heavy chain is in bold.

FIG. 1C. The deduced amino acid sequence (SEQ ID NO:8) and the nucleotide sequence (SEQ ID NO:9) of the light chain variable region (VL) of 3B10. The three complementarity determining regions (CDRs) are underlined, and the first NH2-terminal amino acid residue of the matured light chain is in bold. Position 175 of the nucleotide sequence is either a C or a T. The corresponding amino acid residue is either Phe or Leu.

FIG. 3. The amino acid sequence of the murine PTN-Fc fusion protein (SEQ ID NO: 13). The signal peptide (residues 1-19, derived from an antibody gene) is underlined, the linker sequence (residues 156-160) is dot-underlined and the human Fc region (residues 161-387) is double underlined. The PTN sequence is not underlined.

FIG. 5. The amino acid sequence of PTN-OVA fusion protein (SEQ ID NO: 14) The OVA insertion sequence (SEQ ID NO: 15) is underlined.

FIG. 10. Anti-PTN antibodies inhibit in vitro angiogenesis. HUVEC cells were mixed with supernatant of SW13/PTN cells and plated with (Right) or without (Left) anti-PTN antibodies (5 µg/ml) in 24-well plates that were pre-coated with Matrigel. After 17-20 hours of incubation, the number of tubes was counted under the light microscope.

DETAILED DESCRIPTION OF THE INVENTION

Definitions

Figure 2:
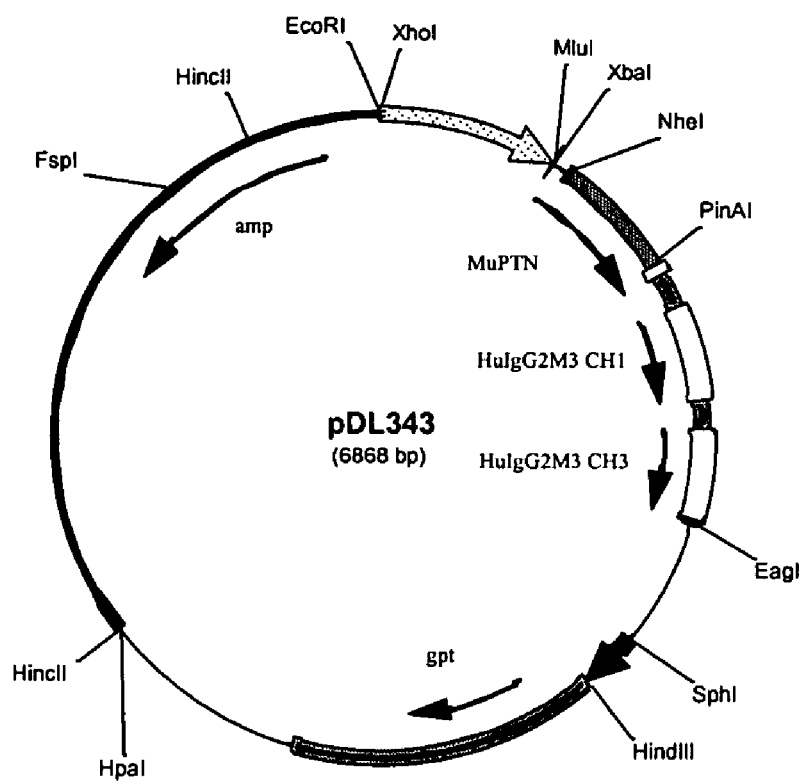
FIG. 2. The plasmid map of pDL343 for the murine PTN-Fc construct

As used herein, the term "antibody" or "immunoglobulin" refers to a protein consisting of one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad immunoglobulin variable V region genes (as indicated below, there are V genes for both H-heavy- and L-light-chains). Full-length immunoglobulin "light chains" (about 25 Kd or 214 amino acids) are encoded by a variable region gene, V-kappa or V-lambda, at the NH2-terminus (about 110 amino acids) and, respectively, a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and (Fab')$_2$, as well as bifunctional hybrid antibodies (e.g., Lanzavecchia et al., Eur. J. Immunol. 17: 105 (1987)) and in single chains (e.g., Huston et al., Proc. Natl. Acad. Sci. U.S.A. 85: 5879-5883 (1988) and Bird et al., Science 242: 423-426 (1988), which are incorporated herein by reference). (See, generally, Hood et al., "Immunology", Benjamin, N.Y., 2nd ed. (1984), and Hunkapiller and Hood, Nature, 323: 15-16 (1986), which are incorporated herein by reference).

A "subject" refers to a vertebrate, preferably a mammal, more preferably a human.

The term "cancer" refers to any type of cancer or neoplasm or malignant tumors found in mammals, including carcinomas, sarcomas, or hematopoietic neoplastic disorders. Examples of cancers include, but are not limited to, Hodgkin's Disease, Non-Hodgkin's Lymphoma, multiple myeloma, leukemia, neuroblastoma, breast cancer, ovarian cancer, lung cancer, cancers of head and neck, cancer of endothelium, cancers of bone, cancers of muscle, pancreatic cancer, rhabdomyosarcoma, primary thrombocytosis, primary macroglobulinemia, small-cell lung tumors, stomach cancer, colon cancer, kidney cancer, malignant pancreatic insulanoma, malignant carcinoid, urinary bladder cancer, melanoma, premalignant skin lesions, testicular cancer, lymphomas, thyroid cancer, esophageal cancer, genitourinary tract cancer, malignant hypercalcemia, cervical cancer, endometrial cancer, epidermal cancer, adrenal cortical cancer, prostate cancer, or uterine cancer. Cancer cells are the cancerous cells of any type of cancers, which can be cells of cancer tissues from a patient or cells of an established cancer cell line.

The term "epitope" refers to any portion (determinant) of a protein that is capable of eliciting an immune response and being specifically bound by an antibody. Epitope determinants usually consist of active surface groupings of molecules such as amino acids or GAG side chains and usually have specific three-dimensional structural characteristics, as well as specific charge characteristics. Two antibodies are said to bind to substantially the same epitope of a protein if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. In conducting an antibody competition study between a control antibody (for example, one of the anti-PTN antibodies described herein) and any test antibody, one may first label the control antibody with a detectable label, such as, biotin, enzymatic, radioactive label, or fluorescence label to enable the subsequent identification. An antibody that binds to substantially the same epitope as the control antibody should be able to compete for binding and thus should reduce control antibody binding, as evidenced by a reduction in bound label.

The term "differentially expressed" means that a polypeptide or a mRNA encoding such a polypeptide is expressed in a type of cells that is cancerous at a higher level than in the same type of cells that is non-cancerous, for example, 30% more, 50% more, 100% more, 200% more, 300% more or 400% more. For instance, if PTN is differentially expressed in breast cancer cells, PTN protein or mRNA will express at a higher level in certain breast cancer cell compared to normal breast cells. The protein expression level can be measured by the standard technology known in the art, such as western blot, ELISA, immunohistological staining, or FACS analysis. The mRNA expression level can be measured by the standard technology known in the art, such as, RT-PCR, Northern blot, RNA protection assay, or in situ hybridization.

The term "derived from" means "obtained from" or "produced by" or "descending from".

The term "genetically altered antibodies" means antibodies wherein the amino acid sequence has been varied from that of a native antibody. Because of the relevance of recombinant DNA techniques to this invention, one need not be confined to the sequences of amino acids found in natural antibodies; antibodies can be redesigned to obtain desired characteristics. The possible variations are many and range from the changing of just one or a few amino acids to the complete redesign of, for example, the variable or constant region. Changes in the constant region will, in general, be made in order to improve or alter characteristics, such as complement fixation, interaction with membranes and other effector functions. Changes in the variable region will be made in order to improve the antigen binding characteristics.

The term "chimeric antibody" refers to an antibody in which the constant region comes from an antibody of one species (typically human) and the variable region comes from an antibody of another species (typically rodent).

As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin. For example, a humanized antibody would not encompass a typical chimeric antibody as defined above, e.g., because the entire variable region of a chimeric antibody is non-human. One says that the donor antibody has been "humanized", by the process of "humanization", because the resultant humanized antibody is expected to bind to the same antigen as the donor antibody that provides the CDR's. See, e.g. Queen et al., U.S. Pat. Nos. 5,530,101; 5,585,089; 5,693,762; and 6,180,370 (each of which is incorporated by reference in its entirety).

The term "an antigen binding fragment of an antibody" refers to any portion of an antibody that retains the binding utility to the antigen. An exemplary antigen-binding fragment of an antibody is the heavy chain and/or light chain CDR, or the heavy and/or light chain variable region.

The term "homologous," in the context of two nucleic acids or polypeptides refers to two or more sequences or subsequences that have at least about 85-90%, most preferably 95% or higher nucleotide or amino acid residue identity, when compared and aligned for maximum correspondence, as measured using the following sequence comparison method and/or by visual inspection. Preferably, the "homolog" exists over a region of the sequences that is preferably about 50 residues in length, more preferably over a region of at least about 100 residues, and most preferably the sequences are substantially identical over at least about 150 residues, or over the full length of the two sequences to be compared.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215:403-410 (1997); blast.wustl.edu/blast/README.htm-1) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported.

The term "PTN" refers to the one or more PTN polypeptides existing in each mammalian species, such as the mouse PTN (mouse version), the rat PTN (rat version), the rabbit PTN (rabbit version), the monkey PTN (monkey version), and the human PTN (human version). An antibody that binds to PTN refers to an antibody that binds to at least one of the polypeptides selected from the group consisting of the mouse PTN, rat PTN, monkey PTN, and human PTN. Preferably, the antibody binds to the human PTN and/or mouse PTN, more preferably, the antibody binds to the human PTN.

The term "host animal" is used to describe animals that have their natural genome unaltered or have their genome genetically and artificially manipulated so as to include the genetic material which is not naturally present within the animal or be deprived of the genetic material which is naturally present within the animal. The host animals are non-human mammalian host animals, for example, mice, hamsters and rats.

I. Antagonists of PTN

The antagonists of PTN include any molecules that directly or indirectly counteract, reduce, or inhibit PTN biological activities. In a preferred embodiment, the antagonists of PTN compete or preferably block the binding of PTN to their receptors, such as ALK. The antagonists should counteract, reduce, or inhibit at least on biological activities of PTN, for example, receptor binding, tyrosine phosphorylation, downstream signal transduction, and the oncogenic or angiogenic activities.

In one aspect, the antagonists directly interact with PTN. Preferably, the antagonists are proteins. More preferably, the proteins bind to PTN, and even more preferably, the antagonists are antibodies or antibody fragments that bind to PTN and neutralize at least one biological activity of PTN.

In another aspect, the antagonists are any polypeptides or peptides that inhibit PTN activities but do not directly interact with PTN. For example, the antagonists can be mutated PTN molecules, such as dominant-negative mutants derived from a wild-type PTN by terminal truncations or amino acid substitutions. Preferably such mutated PTNs retain the binding ability to the signaling molecules of PTN but lose the ability of triggering the downstream signaling transduction of PTN. Therefore, the mutated PTN molecules can compete with the wild-type PTN and thus block the activities of the wild-type PTN. The standard mutagenesis and molecular cloning techniques can accomplish the terminal truncation and amino acid substitution. The mutated PTN molecules can be administered into the target cells by standard delivery means known in the art, such as, lipid or viral transfections. Additional examples are the blocking peptides or polypeptides that block the ligand-binding site of PTN with its receptors. In one example, such blocking polypeptides are the antibodies against the receptors of PTN, for example, anti-ALK antibodies.

Alternatively, the antagonists interact with and regulate the up-stream or downstream components of the PTN signaling pathway and indirectly reduce the activities of PTN. For example, it is known that PTN activities are mediated through the receptor tyrosine kinase pathway upon its binding to its receptors, such as ALK. Accordingly, any molecules capable of regulating this pathway can be candidate antagonists, including, but not limited to, the antibodies or other antagonist blocking the binding and activities of these components. Yeast two-hybrid and variant screens offer preferred methods for identifying endogenous additional interacting proteins of the components of the PTN signaling pathways (Finley, R. L. et al. in DNA Cloning-Expression Systems: A Practical Approach, eds. Glover D. & Hames B. D. (Oxford University Press, Oxford, England), pp. 169-203 (1996); Fashema S. F. et al., Gene 250: 1-14 (2000); Drees B. L., CUK Opin Chem Biol 3: 64-70 (1999); Vidal M. and Legrain P. Nucleic Acids. Res. 27:9191-29 (1999); and U.S. Pat. No. 5,928,868). Mass spectrometry is an alternative method for the elucidation of protein complexes (reviewed in, e. g., Pand ley A and Mann M, Nature 405: 837-846 (2000); Yates J R 3rd, Trends Genet 16: 5-8 (2000)).

In yet another aspect, the antagonists should inhibit the protein expression of PTN. PTN expression can be regulated at the level of transcription, such as, by a regulator of transcription factors of PTN, or at the level of mRNA splicing, translation or post-translation.

The antagonists can also be nucleic acids, including, but not limited to, anti-sense nucleic acids of the nucleic acid sequence encoding part or full or having substantial sequence similarity of PTN. The DNA sequence of PTN is known in the art and disclosed herein. Subsequently, anti-sense nucleic acid probes of DNAs encoding PTN, and the optimal condition of the anti-sense blocking can be developed by using the related techniques known to a skilled artisan in the field of molecular biology. Similarly, the nucleic acid reagent may belong to the class of short interfering RNA or siRNA.

The antagonists can also be ribozymes, which refer to an RNA based enzyme capable of targeting and cleaving particular base sequences in DNA and RNA. Ribozymes either can be targeted directly to cells, in a form of RNA oligonucleotides incorporating ribozyme sequences or introduced into cell as expression construct encoding the desired ribozyme RNA. The methods of delivering the ribozyme RNAs are known in the art.

The antagonists of the present invention also include small molecules, which often modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500 daltons. This class of antagonists includes chemically synthesized molecules, for instance, compounds from combinatorial chemical libraries. Synthetic compounds may be rationally designed or identified based on known or inferred properties of the PTN protein or may be identified by screening compound libraries. Alternative appropriate antagonists of this class are natural products, particularly secondary metabolites from organisms such as plants or fungi, which can also be identified by screening compound libraries for PTN-modulating activity. Methods for generating and obtaining compounds are well known in the art (Schreiber S L, Science 151: 1964-1969 (2000); Radmann J. and Gunther J., Science 151: 1947-1948 (2000)).

For the purpose of the present invention, the antagonists of PTN also include the antagonists of the receptors of PTN as long as these receptor antagonists inhibit the biological activities of PTN ligand-receptor pairs. These receptor antagonists inhibit the activities of at least one of the receptors of PTN, including antibodies against one of the PTN receptors, dominant-negative mutants, transcription regulators, anti-sense nucleic acid molecules, ribozyme RNA molecules, or small molecule inhibitors of at least one PTN receptors. One exemplary PTN receptor is ALK. Additional PTN receptors can be identified and obtained via the standard techniques used in molecular biology and cell biology. For example, the PTN polypeptides, preferably receptor binding domains, may be used as a probe to screen a protein expression library in seeking novel PTN receptors.

II. Antibodies to PTN

The antibodies against PTN of the present invention may be in a polyclonal or monoclonal form and should bind to at least one epitope of PTN, preferably a human PTN and/or mouse PTN. The antibodies should bind to a) a full-length PTN polypeptide, or b) a functionally active fragment or derivative thereof.

SEQ ID NOs: 1 and 2 depict the amino acid sequences of the full-length wild-type human and mouse PTN, respectively. A "functionally active" PTN fragment or derivative exhibits one or more functional activities associated with a full-length, wild-type PTN protein, such as antigenic or immunogenic activity, ability to bind natural cellular substrates, etc. The functional activity of PTN proteins, derivatives and fragments can be assayed by various methods known to one skilled in the art (Current Protocols in Protein Science, Coligan et al., eds., John Wiley & Sons, Inc., Somerset, N.J. (1998)). For purposes herein, functionally active fragments also include those fragments that comprise one or more structural domains of a PTN polypeptide, such as a binding domain. Protein domains can be identified using the PFAM program (Bateman A., et al., Nucleic Acids Res. 27: 260-2 (1999); pfam.wustl.edu).

PTN polypeptide derivatives typically share a certain degree of sequence identity or sequence similarity with SEQ ID NO: 1 or 2, or a fragment thereof. PTN derivatives can be produced by various methods known in the art. The manipulations that result in their production can occur at the gene or protein level. For example, a cloned PTN gene sequence can be cleaved at appropriate sites with restriction endonuclease(s) (Wells et al., Philos. Trans. R. Sot. London SerA 317: 415 (1986)), followed by further enzymatic modification, if desired; isolated, and ligated in vitro, and expressed to produce the desired derivative. Alternatively, a PTN gene can be mutated in vitro or in vivo, to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. 13: 4331 (1986)), use of TAB® linkers (available from Pharmacia and Upjohn, Kalamazoo, Mich.), etc.

The anti-PTN antibodies of the present invention include antibodies having all types of constant regions, including IgM, IgG, IgD, IgA and IgE, and any isotype, including IgG1, IgG2a, IgG2b, IgG3 and IgG4. The light chains of the antibodies can either be kappa light chains or lambda light chains.

In a preferred aspect, anti-PTN antibodies preferably bind to a PTN epitope at a binding affinity of at least $10^6 M^{-1}$, $10^7 M^{-1}$, $10^8 M^{-1}$, $10^9 M^{-1}$ or $10 M^{-1}$.

In another preferred aspect, the antibodies of the present invention neutralize at least one, or preferably all, biological activities of PTN. The biological activities of PTN include: 1) receptor binding activities (for instance, these neutralizing antibodies should be capable of competing with or completely blocking the binding of PTN to at least one, and preferably all, of its receptors, such as ALK.); 2) signaling transduction activities, such as receptor dimerization, tyrosine phosphorylation or PI3 kinase phosphorylation; and 3) cellular responses induced by PTN, such as oncogenic activities (PTN-mediated cancer cell proliferation), and/or angiogenic activities The antibodies of the present invention should have at least one activity selected from the group consisting of: 1) inhibiting cancer cell growth; 2) inhibiting cancer cell survival; 3) inhibiting angiogenesis; 4) inhibiting cancer cell adhesion, migration or invasion; and 5) inducing lysis of cancer cells.

In one preferred embodiment, the antibodies inhibit the growth of cancer cells in vitro (such as in a cell culture) or in vivo (such as in a subject), preferably by at least 10%, 25%, or 50%. The exemplary antibodies that inhibit the cancer cell growth include, but are not limited to, monoclonal antibodies produced by the hybridoma cell lines 3B10, 4B2, 10, 17, 24, 25, 26, 27, 31, 41, 50, 60, 87, 3-4A, 3-11F (see Table 2). 3B10 is an exemplary antibody that inhibits cancer cell growth in a subject by more than 25%, and preferably by about 40%. Hybridoma cell line 3B10, which produces the 3B10 antibody, was deposited on Jul. 13, 2010 with the American Type Culture Collection (ATCC), 10801 University Blvd., Manassas, Va. 20110-2209, USA, and assigned ATCC deposit designation PTA-11180.

In another preferred embodiment, the antibodies inhibit the proliferation of cancer cells, preferably by at least 10%, 25%, 50%, 75%, or 90%. In one example, the cancer cells are cells of glioblastoma, such as U87MG cells. The exemplary antibodies that inhibit the cancer cell proliferation include, but are not limited to, monoclonal antibodies produced by the hybridoma cell lines 3B10, 4B2, 10, 17, 24, 25, 26, 27, 31, 41, 50, 60, 87, 3-4A, 3-11F (see Table 2). The exemplary antibodies that inhibit the cancer cell proliferation by at least 50% include, but are not limited to, monoclonal antibodies produced by the hybridoma cell lines: 3B10, 4B2, 10, 25, 27, 50, 60, 87, 3-4A, 3-11F. The exemplary antibodies that inhibit cancer cell proliferation by at least 75% include, but are not limited to, monoclonal antibodies produced by the hybridoma cell line 10.

In another aspect, the antibodies can inhibit the anchorage independent growth (colony formation) of cancer cells, preferably by at least 10%, 25%, 50%, 75%, or 90%. The non-limiting examples of the cancer cells include, but are not limited to, cancer cells of adrenal carcinoma. The cancer cells can be cells from the patient cancer tissues or cells of an established cancer cell lines, such as SW13 cells. The exemplary antibodies that inhibit the anchorage independent growth of cancer cells include, but are not limited to, monoclonal antibodies produced by the hybridoma cell lines 3B10 (complete inhibition), 4B2 (at least 75%), 24 (at least 50%), 87 (at least 50%), and 31 (at least 25%).

In yet another preferred embodiment, the antibodies inhibit angiogenesis, preferably by at least 10%, 25%, or 50%. Angiogenesis is preferably induced by cancer cells. The exemplary antibodies that inhibit angiogenesis include, but are not limited to, monoclonal antibodies produced by the hybridoma cell lines 25 (at least 50%), 27 (at least 50%), 31 (at least 25%), and 3-11F (at least 50%).

The deduced amino acid sequence and the nucleotide sequence of the mature heavy chain variable region of the antibody 3B10 are presented here in SEQ ID NOs:3 and 4, respectively (FIG. 1B). The amino acid sequences of the three complementarity determining regions (CDRs) are SHWMN (SEQ ID NO:5), RIYPGDGDSLYNGKFKG (SEQ ID NO:6), and TRAYGPAWFAY (SEQ ID NO:7).

The deduced amino acid sequence and the nucleotide sequence of the mature light chain variable region of the antibody 3B10 are presented here in SEQ ID NOs:8 and 9, respectively (FIG. 1C). The amino acid sequence of the light chain three complementarity determining regions (CDRs) comprises RSSQSLLDSNNQKNYLA (SEQ ID NO:10), ASIRES (SEQ ID NO:11), and QQHYSTPLT (SEQ ID NO:12).

The present invention provides for a polypeptide comprising an amino acid sequence of SEQ ID NOs:3, 5, 6, 7, 8, 10, 11, or, 12.

The present invention provides for antibodies comprising a mature heavy chain variable region comprising an amino acid sequence of SEQ ID NO:3, and/or a mature heavy chain variable region comprising an amino acid sequence of SEQ ID NO:8

The present invention provides for a heavy chain CDR or heavy chain CDRs of an antibody comprising an amino acid sequence of SEQ ID NOs: 5, 6, and/or 7, or a light chain CDR or light chain CDRs of an antibody comprising an amino acid sequence of SEQ ID NOs: 10, 11, and/or 12.

The present invention includes the analogs of the antibodies or antibody fragments describes herein. Preferred analogs include a) the CDRs comprising an amino acid sequences sharing at least 60%, 80% or 90-95% amino acid sequence identity with SEQ ID NOs: 5, 6, 7, 10, 11, or 12; b) mature heavy and light chain variable region comprising an amino acid sequence sharing at least 60%, 80% or 90-95% amino acid sequence identity with SEQ ID NOs: 3 and 8, respectively; and c) antibodies or antibody fragments comprising these heavy and/or chain variable regions and/or CDRs. More preferred analogs of exemplified antibodies differ from exemplified antibodies or antibody fragments by conservative amino acid substitutions. For purposes of classifying amino acids substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another. The analogs of the present invention can be made by amino acid substitutions via mutagenesis methods known in the art.

The present invention provides for the polynucleotide molecules encoding the antibodies and antibody fragments and their analogs described herein. Because of the degeneracy of the genetic code, a variety of nucleic acid sequences encode each antibody amino acid sequence. The desired nucleic acid sequences can be produced by de novo solid-phase DNA synthesis or by PCR mutagenesis of an earlier prepared variant of the desired polynucleotide. In a preferred embodiment, the codons that are used comprise those that are typical for human or mouse (see, e.g., Nakamura, Y., Nucleic Acids Res. 28: 292 (2000)). The present invention provides for the polynucleotide molecules encoding the antibodies and antibody fragments and their analogs described herein, for example, the polynucleotide molecules comprising SEQ ID NOs: 4 or 9.

The present invention includes the monoclonal antibodies that bind to substantially the same epitope as any one of these above-exemplified antibodies. Our investigation has discovered that a full-length wild-type PTN polypeptide comprises at least three types of epitopes: Type I, Type II, and Type III. Type I (also called AL1) is the epitope that antibody AL1 binds to. Type II (also called AL12/AL13) is the epitope that antibody AL12 binds to. Type III is the epitope that is different from Type I and II. Most of the neutralizing antibodies, including the antibody produced by the hybridoma 3B10, bind to a Type III epitope.

Antibodies against PTN of all species of origins are included in the present invention. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. In a preferred embodiment, the antibody is an isolated monoclonal antibody that binds to and/or neutralizes PTN.

The monoclonal antibodies are produced by the methods of the present invention (see below). The present invention produced more than 100 monoclonal antibodies against PTN (see Examples). The exemplary anti-PTN monoclonal antibodies are antibodies produced by the hybridomas: 3B10, 4B2, 10, 17, 24, 25, 26, 27, 31, 41, 50, 60, 87, 3-4A, 3-11F (Table 2) (which may also be called antibodies: 3B10, 4B2, 10, 17, 24, 25, 26, 27, 31, 41, 50, 60, 87, 3-4A, 3-11F).

The polyclonal forms of the anti-PTN antibodies are also included in the present invention. Preferably, these antibodies neutralize at least one activity of PTN, or bind to the same epitopes as the described monoclonal antibodies in the present invention. Polyclonal antibodies can be produced by the method described herein (see below).

Recombinant antibodies against PTN are also included in the present invention. These recombinant antibodies have the same amino acid sequence as the natural antibodies or have altered amino acid sequences of the natural antibodies in the present invention. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

The genetically altered anti-PTN antibodies should be functionally equivalent to the above-mentioned natural antibodies. Modified antibodies providing improved stability or/and therapeutic efficacy are preferred. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this invention can be modified post-translationally (e.g., acetylation, and/or phosphorylation) or can be modified synthetically (e.g., the attachment of a labeling group). Preferred genetically altered antibodies are chimeric antibodies and humanized antibodies.

The chimeric antibody is an antibody having a variable region and a constant region derived from two different antibodies, preferably derived from separate species. Preferably, the variable region of the chimeric antibody is derived from murine and the constant region is derived from human.

In one embodiment, the murine variable regions are derived from any one of the monoclonal antibodies described herein, including the non-limiting examples: (a) antibodies: 3B10, 4B2, 10, 17, 24, 25, 26, 27, 31, 41, 50, 60, 87, 3-4A, and 3-11F (Table 2); and/or (b) the antibodies that bind to substantially the same epitope as any one of the antibodies of (a).

In another embodiment, the murine variable regions are (a) variable regions comprising an amino acid sequence of SEQ ID NOs: 3 and/or 8; (b) any analogs of the variable regions of (a); and/or (c) the variable regions that bind to substantially the same epitope as any one of the antibodies comprising the variable regions of (a).

In order to produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. No. 5,677,427; U.S. Pat. No. 6,120,767; and U.S. Pat. No. 6,329,508, each of which is incorporated by reference in its entirety.

The genetically altered antibodies used in the present invention include humanized antibodies that bind to and neutralize PTN. In one embodiment, said humanized antibody comprising CDRs of a mouse donor immunoglobulin and heavy chain and light chain frameworks and constant regions of a human acceptor immunoglobulin. In one example, the humanized antibodies are the humanized versions of: (a) antibodies: 3B10, 4B2, 10, 17, 24, 25, 26, 27, 31, 41, 50, 60, 87, 3-4A, and 3-11F (Table 2); and/or (b) the antibodies that bind to substantially the same epitope as any one of the antibodies of (a). In another example, the humanized antibodies are the humanized versions of: (a) antibodies comprising an amino acid sequence of SEQ ID NOs: 3 and/or 8; (b) any analogs of the antibodies of (a); and/or (c) the antibodies that bind to substantially the same epitope as the antibodies of (a). In a preferred embodiment, the humanized antibodies comprise heavy chain CDRs comprising an amino acid sequence of SEQ ID NOs: 5, 6, 7, 10, 11, and/or, 12. The method of making humanized antibody is disclosed in U.S. Pat. Nos. 5,530,101; 5,585,089; 5,693,761; 5,693,762; and 6,180,370 each of which is incorporated herein by reference in its entirety.

Anti-PTN fully human antibodies are also included in the present invention. In a preferred embodiment of the present invention, said fully human antibodies neutralize the activities of PTN described herein.

Fully human antibodies against PTN are produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety)

Human antibodies against PTN can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, One approach is to screen a DNA library from human B cells according to the general protocol outlined by Huse et al., Science 246:1275-1281 (1989). Antibodies binding PTN or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety). In these methods, libraries of phage are produced in which members display different antibodies on their outer surfaces. Antibodies are usually displayed as Fv or Fab fragments. Phage displaying antibodies with a desired specificity are selected by affinity enrichment to PTN or fragment thereof.

Eukaryotic ribosome can also be used as means to display a library of antibodies and isolate the binding human antibodies by screening against the target antigen, such as PTN, as described in Coia G, et al., J. Immunol. Methods 1: 254 (1-2):191-7 (2001); Hanes J. et al., Nat. Biotechnol. 18(12): 1287-92 (2000); Proc. Natl. Acad. Sci. U.S.A. 95(24):14130-5 (1998); Proc. Natl. Acad. Sci. U.S.A. 94(10): 4937-42 (1997), each which in incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via yeast two-hybrid system (WO0200729A2, which is incorporated by reference in its entirety).

Fragments of the anti-PTN antibodies, which retain the binding specificity to PTN, are also included in the present invention. Examples of these antigen-binding fragments include, but are not limited to, partial or full heavy chains or light chains, variable regions, or CDR regions of any anti-PTN antibodies described herein.

In a preferred embodiment of the invention, the antibody fragments are truncated chains (truncated at the carboxyl end). Preferably, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemistry techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining $V_L$ and $V_H$-coding regions with a DNA that encodes a peptide linker connecting the VL and VH protein fragments Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins (e.g., immunotoxins) or conjugates having novel properties.

The present invention comprises the use of anti-PTN antibodies in immunotoxins. Conjugates that are immunotoxins including antibodies have been widely described in the art. The toxins may be coupled to the antibodies by conventional coupling techniques or immunotoxins containing protein toxin portions can be produced as fusion proteins. The conjugates of the present invention can be used in a corresponding way to obtain such immunotoxins. Illustrative of such immunotoxins are those described by Byers, B. S. et al., Seminars Cell Biol 2:59-70 (1991) and by Fanger, M. W. et al., Immunol Today 12:51-54 (1991).

Recombinant DNA techniques can be used to produce the recombinant anti-PTN antibodies, as well as the chimeric or humanized anti-PTN antibodies or any other anti-PTN genetically-altered antibodies and the fragments or conjugate thereof in any expression systems including both prokaryotic and eukaryotic expression systems, such as bacteria, yeast, insect cells, plant cells, mammalian cells (for example, NS0 cells).

Once produced, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extra corporeally) or in developing and performing assay procedures, immunofluorescent stainings, and the like. (See, generally, Immunological Methods, Vols. I and II (Lefkovits and Pernis, eds., Academic Press, NY, 1979 and 1981).

Antibodies against the receptors of PTN (such as ALK) are also encompassed in the present invention. These antibodies are natural antibodies, recombinant antibodies, humanized antibodies, chimeric antibodies, the fully human antibodies, antibody fragments and conjugates. Preferably, these antibodies are capable of neutralizing the biological activities of the PTN ligand-receptor pairs. These neutralizing antibodies are considered as antagonists of PTN for the purpose of the present invention. These antibodies can be made in the similar fashion as the making of the anti-PTN antibodies, and the fragments and conjugates thereof described herein.

III. Methods of Making Antibodies

The present invention provides for a method of producing an antibody against a protein.

The method of producing an isolated antibody against a protein comprises 1) selecting a host animal; 2) immunizing said host animal with a fusion protein comprising said protein connected with a T-cell epitope. A "T-cell epitope" is defined as a peptide sequence recognized by the T-cell receptor of T helper cells in the context of MHC molecules. Upon binding to one or more of these T-cell epitopes, the T helper cells can be activated and recruit T-cells. The present methods can use any T-cell epitopes known in the art, for example, OVA and cytochrome C peptide. Additional examples are the T-cell epitopes disclosed in U.S. Pat. Nos. 6,143,935, 5,785,973, and 6,419,931. The T-cell epitopes can be connected to the C-terminus or N-terminus of said protein, or inserted in the suitable positions between N-terminus and C-terminus of said protein as long as the connection will not detrimentally affect either the antigenic utility of said protein or the binding utility of the T-cell epitopes with T helper cells. In one example, where the antibodies against PTN are intended to be made, the N-terminus of OVA peptide can be inserted after position 124 of SEQ ID NO: 1. Standard molecular cloning techniques are used to link a DNA molecule encoding a T-cell epitope to a DNA molecule encoding said antigenic protein, so that a DNA molecule encoding the fusion protein is created. Expression vectors comprising the DNA molecules encoding the fusion protein are then transfected to any expression systems to produce the desired fusion protein. The expression systems include both prokaryotic and eukaryotic expression systems, such as bacteria, yeast, insect cells, plant cells, and mammalian cells.

When the above-described methods are used to produce monoclonal antibodies, hybridoma methodology will follow after immunization, as described originally by Kohler and Milstein, Nature 256: 495-7 (1975); Eur. J. Immunol. 6: 511 (1976)). Accordingly, the method will further comprise the steps of: 3) isolating a lymphoid cell from said immunized host animal; 4) fusing said lymphoid cell to a myeloma cell, so that a hybrid cell is created; 5) cultivating said hybrid cell; and 6) isolating a monoclonal antibody.

Lymphoid cells from the immunized host animal are fused with myeloma cells to generate a hybrid cell line that can be cultivated and subcultivated indefinitely, to produce large quantities of monoclonal antibodies.

The hybrid cell lines can be maintained in vitro in cell culture media. The cell lines of this invention can be selected and/or maintained in a composition comprising the continuous cell line in the known hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is isolated from tissue culture supernatant by conventional methods such as precipitation, ion exchange chromatography, affinity chromatography, or the like.

Alternatively, when the above-described methods are used for producing polyclonal antibodies, then following immunization, the polyclonal antibodies which secreted into the bloodstream can be recovered using known techniques. Purified forms of these antibodies can, of course, be readily prepared by standard purification techniques, preferably including affinity chromatography with Protein A, anti-immunoglobulin, or the antigen itself. In any case, in order to monitor the success of immunization, the antibody levels with respect to the antigen in serum will be monitored using standard techniques such as ELISA, RIA and the like.

Although the above-mentioned methods can be utilized to make antibodies against any proteins, they are particularly useful in making antibodies against proteins that are highly homologous among the mammalian species, preferably between a human and a rodent (a mouse or a rat).

Where proteins are highly homologous among the mammalian species, for the purpose of the present invention, the proteins typically a) exist in at least two mammalian species, preferably, in a rodent and a human; and b) the version of the proteins in each species, such as the mouse version and the human version, are highly homologous to each other. The term "highly homologous" refers to two polypeptides or two nucleic acid molecules share more than 90%, or 95%, 99%, or even about 100% amino acid sequence identity. In one example, such highly homologous proteins are PTNs (human PTN and mouse PTN), which are nearly identical among mammalian species. As shown in FIG. 1, the human version of PTN (human PTN) and the mouse version of PTN-(mouse PTN) have more than 99% sequence identity.

The present invention provides for the isolated antibodies that are produced by the methods described herein.

The methods of the present invention offer at least two advantages as compared to the conventional methods of making polyclonal and monoclonal antibodies. First, the present methods can produce antibodies, especially neutralizing antibodies against proteins that are highly homologous among the mammalian species. The highly homologous proteins usually play key roles in important physiological pathways in mammals including human. Unfortunately, it is very difficult to elicit the immune response of these proteins in a rodent. The present methods have opened a new avenue for the immunotherapy targeted to these proteins. Second, it is desirable in the clinical studies to produce an antibody that binds to a target antigen of human as well as that of other mammalian species (e.g., mouse, rat, rabbit, etc.), which will be used in a pre-clinical disease model. Such an antibody can thus be used for both pre-clinical studies with a model animal and for clinical studies with humans, saving a great deal of time and resources in the drug development process. The antibodies produced by the present methods will preferably have such characteristics.

In addition to the above-described methods, anti-PTN antibodies can also be made via PTN immunization of a host animal that has a defect in the immune system of said host animal so that the host animal has a reduced ability to produce autoantibodies compared to the host animal without said defect. The term "autoantibodies" have a clear and definite meaning to the one skilled in the art, which refers to the antibodies that react non-specifically to common "self" protein and DNA. They are believed to cause autoimmune reactions in patients. Various kinds of host animals that have a defect in the immune system and a reduced ability of producing autoantibody are known in the art. Many of them are commercially available and can be purchased from the Jackson Laboratory. In one example, these host animals are the strains of autoimmune mice (mice having autoimmune diseases). Examples of such autoimmune mice are NOD/LtJ (cat # 0001976), B6. MRL-Tnfrsf6lpr (cat # 000482), and NZB/W F1/J (cat# 100008) from Jackson Laboratory, Bar Harbor, Me. The experimental details of this method are disclosed in the following Examples.

Furthermore, the anti-PTN antibodies can also be produced via PTN immunization of a transgenic mouse lacking the genes encoding mouse PTN in their genomes (a PTN knock-out mouse), which has been developed by Amt et al., Mol. Cell. Neuro. 17: 1014-1024 (2001). The experimental details of this method are disclosed in the following Examples.

IV. Therapeutic Uses

1. Inhibition of Cancer Cell Growth

The present invention is directed to a method of neutralizing at least one biological activity of PTN in a subject in need thereof comprising administering to said subject an effective amount of an antagonist of PTN, wherein said antagonist is a polypeptide.

The present invention includes a method of inhibiting the proliferation or anchorage-independent growth of cancer cells comprising contacting cancer cells with an antagonist of PTN. The antagonists may contact cancer cells in vitro, ex vivo or in vivo (for example, in a subject). In a preferred embodiment, the antagonists are anti-PTN antibodies including the antibodies, antibody fragments, and antibody conjugates of the present invention. Such an inhibition reduces the cancer cell proliferation or anchorage independent growth by at least 10%, 25%, 50%, 75%, or 90%.

The present invention provides for a method of inhibiting the growth of cancer cells in a subject comprising administering an effective amount of an antagonist of PTN into the subject. The inhibition should reduce or prevent the growth of the cancer cells of said subject, preferably by at least 10%, 25%, 35%, or about 40%. As a result, where the cancer is a solid tumor, the inhibition should reduce the size of the solid tumor by at least 10%, 25%, 35%, or about 40%. The subject should a vertebrate, preferably a mammal, and more preferably, a human.

The inhibition of the cancer cell proliferation can be measured by cell-based assays, such as bromodeoxyuridine (BRDU) incorporation (Hoshino et al., Int. J. Cancer 38, 369 (1986); Campana et al., J. Immunol. Meth. 107:79 (1988)); [$^3$H]-thymidine incorporation (Chen, J., Oncogene 13:1395-403 (1996); Jeoung, J., J. Biol. Chem. 270:18367-73 (1995); the dye Alamar Blue (available from Biosource International) (Voytik-Harbin S L et al., In Vitro Cell Dev Biol Anim 34:239-46 (1998)). The anchorage independent growth of cancer cells is assessed by colony formation assay in soft agar, such as by counting the number of cancer cell colony formed on top of the soft agar (see Examples and Sambrook et al., Molecular Cloning, Cold Spring Harbor, 1989).

The inhibition of cancer cell growth in a subject is assessed by monitoring the cancer growth in a subject, for example in an animal model or in human patients. One exemplary monitoring method is tumorigenicity assays. In one example, a xenograft comprises human cells from a pre-existing tumor or from a tumor cell line. Tumor xenograft assays are known in the art and described herein (see, e.g., Ogawa, K., et al., Oncogene 19:6043-6052 (2000)). In another preferred embodiment, tumorigenicity is monitored using the hollow fiber assay, which is described in U.S. Pat. No. 5,698,413, which is incorporated herein by reference in its entirety.

The percentage of the inhibition is calculated by comparing the cancer cell proliferation, anchorage independent growth, or cancer cell growth under antagonist treatment with that under negative control condition (typically without antagonist treatment). For example, where the number of cancer cells or cancer cell colonies (colony formation assay), or PRDU or [$^3$H]-thymidine incorporation is A (under the treatment of antagonists) and C (under negative control condition), the percentage of inhibition would be (C-A)/C× 100%.

2. Inhibition of Angiogenesis

Angiogenesis, the formation of new capillaries from pre-existing vessels, is essential for tumor progression (Folkman, et al., J. Bio. Chem. 267: 10931-10934 (1992)). The induction of angiogenesis is mediated by several angiogenic molecules released by tumor cells, tumor associated endothelial cells and the normal cells surrounding the tumor endothelial cells. The prevascular stage of a tumor is associated with local benign tumors, whereas the vascular stage is associated with tumors capable of metastasizing. Moreover, studies using light microscopy and immunohistochemistry concluded that the number and density of microvessels in different human cancers directly correlate with their potential to invade and produce metastasis. The inhibition of angiogenesis prevents the growth of tumor endothelial cells at both the primary and secondary sites and thus can prevent the emergence of metastases.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

The present invention provides for a method of inhibiting angiogenesis comprising contacting endothelial cells with an effective amount of an antagonist of PTN. Preferably, said angiogenesis is induced by cancer cells. The antagonists may contact endothelial cells in vitro, ex vivo or in vivo (for example, in a subject).

In a preferred embodiment, the present invention provides for a method of inhibiting angiogenesis of a subject comprising administering an effective amount of an antagonist of PTN described herein to said subject.

In another preferred embodiment, the present invention provides for a method of inhibiting metastasis of cancer in a subject comprising administering an effective amount of an antagonist of PTN described herein to said subject.

The inhibition of angiogenesis can be examined via in vitro cell-based assays known in the art, such as the tube formation assay, or in vivo animal model assays known in the art and described in following Examples.

The inhibition of metastasis can be assessed in in vivo animal metastasis model, which is described in detail in the following Examples.

In addition to the inhibition of cancer growth, angiogenesis, and cancer cell metastasis, the PTN antagonists of the present invention may also be able to inhibit adhesion, migration or invasion of cancer cells of cancer cells via contacting the cancer cells with the PTN antagonists of the present invention.

The antagonists may also inhibit the survival of cancer cells or induce cancer cell apoptosis. Cancer cell survival can be assessed by counting the number of living cancer cells. Induction of apoptosis can be measured by the various ways known in the art, such as by flow cytometry with FITC-conjugated annexin V and propidium iodide or terminal deoxynucleotidyl transferase-mediated digoxigenin-11-dUTP nick end labeling (TUNEL) assay (Lazebnik et al., Nature: 371, 346 (1994), (Yonehara et al., J. Exp. Med. 169, 1747 (1989)).

The anti-PTN antibodies of the present invention may be of a subclass or isotype that is capable of mediating the cytolysis of tumor cells to which the antibody molecule binds to, the anti-PTN antibodies induce the antibody dependent cellular cytotoxicity (ADCC). The antibodies should be of subclass IgG3, IgG2a or IgG2b where the antibodies are mouse immunoglobulins, and IgG1 where the antibody are human immunoglobulins.

Antagonists of the present invention are useful for the treatment of cancer. The present invention provides for a method of treating or preventing a cancer comprising administering to a subject in need of such treatment or prevention of an effective amount of an antagonist of PTN, preferably an anti-PTN antibody. The anti-PTN antibodies include the antibodies, antibody fragments, and antibody conjugates of the present invention. Such prevention or treatment comprises inhibiting, reversing cancer cell growth, or metastasis, or reducing the size of cancer in a subject.

Therapeutic methods are usually applied to human patients but may be applied to other mammals.

There are various methods of administering the PTN antagonists, for example, antibodies of the present invention. Parenteral administration is preferred. The antagonists may be administered to a patient intravenously as a bolus or by continuous infusion over a period of time; or by intramuscular, subcutaneous, intraperitoneal, or intra-cerebrospinal routes. Oral, topical, inhalation routes, or other delivery means known to those skilled in the art are also included in the present invention.

The pharmaceutical compositions of the present invention commonly comprise a solution of antagonists (for example, antibodies), or a cocktail thereof dissolved in an acceptable carrier, preferably an aqueous carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein. The concentration of an antagonist (for example, antibody) in these formulations varies widely from about 0.1 to 100 mg/ml but is often in the range 1 to 10 mg/ml. The formulated monoclonal antibody is particularly suitable for parenteral administration, and can be administered as an intravenous infusion or by subcutaneous, intramuscular or intravenous injection. Actual methods for preparing parentally administrable compositions are known or apparent to those skilled in the art and are described in more detail in, for example, Remington's Pharmaceutical Science (15th Ed., Mack Publishing Company, Easton, Pa., 1980), which is incorporated herein by reference. The present invention provides for a pharmaceutical composition comprising an antagonist of PTN, preferably, an antibody that binds to PTN.

The compositions can be administered for prophylactic and/or therapeutic treatments. An amount adequate to accomplish the desired effect is defined as an "effective amount". The antagonists (such as antibodies) can be delivered into a patient by single or multiple administrations. Doses of the drug will typically contain from 0.01 to 100 mg antagonist (for example, antibody or antibody conjugate) but most often from 0.1 to 1, or 1, 2 or 5 to 20 mg per kilogram body weight or as a unit dose, in an amount sufficient to alleviate the disease without causing unacceptable side effects ("effective amount"). The antibody drug may be administered once or multiple times, e.g., 1, 2 or 3 times per day, week or month for one to several days, weeks, months or years, or chronically, depending upon the nature and severity of the disease and the discretion of the attending physician.

For the purpose of treatment of disease, the appropriate dosage of the antagonists (for example, antibodies) will depend on the severity and course of disease, the patient's clinical history and response, the toxicity of the antibodies, and the discretion of the attending physician. The initial candidate dosage may be administered to a patient. The proper dosage and treatment regimen can be established by monitoring the progress of therapy using conventional techniques known to the people skilled of the art.

Additionally, the antagonist (such as antibodies) can be utilized alone in substantially pure form, or together with therapeutic agents, as are known to those of skill in the art (see, e.g., Cancer: Principles and Practice of Oncology, 5$^{th}$ ed., Devita et al., Lippincott-Ravel Publishers, 1997). Other therapies that may be used in conjunction with treatment with the antibodies include administration of anti-sense nucleic acid molecules or biologicals, such as additional therapeutic antibodies. Thus, the treatment of the present invention is formulated in a manner allowing it to be administered serially or in combination with another agent for the treatment of cancer or psoriasis. For the treatment of cancer, the conventional therapeutic methods for cancer therapy, such as chemotherapy, radiation therapy and surgery can be used together with the antagonists of the present invention.

V. Diagnostic Methods

Antibodies disclosed herein are useful in diagnostic and prognostic evaluation of diseases and disorders, particularly cancers associated with PTN expression. At each stage of disease, monoclonal antibodies may be used to improve diagnostic accuracy and facilitate treatment decisions. Unlike standard diagnostic methods for tumors and cancer, such as computed topographic (CT) scans, which depend on a change in size or architecture of organs or lymph nodes, labeled monoclonals can detect abnormal cells at an early stage, because of their expression of tumor antigens, such as PTN. Once cancer is diagnosed, accurate staging is important in deciding on the most appropriate therapy. Later, during follow-up of surgery, rising serum levels of tumor antigens may indicate recurrence before it can be detected by conventional methods.

Methods of diagnosis can be performed in vitro using a cellular sample (e.g., blood sample, lymph node biopsy or tissue) from a patient or can be performed by in vivo imaging.

In particular embodiments, the present invention provides an antibody conjugate wherein the antibodies of the present invention are conjugated to a diagnostic imaging agent. Compositions comprising the antibodies of the present invention can be used to detect PTN, for example, by radioimmunoassay, ELISA, FACS, etc. One or more labeling moieties can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

The present invention provides for a method of detecting a cancer comprising detecting the differential expression of mRNA or protein of PTN in said cancer cells in a subject in need of such detection. In one exemplary embodiment, the method of detecting cancer comprising: a) isolating a sample from a patient; b) contacting cells of said sample with the antibodies of the present invention; c) contact non-cancerous cells of the same type of said sample cells with the antibodies of the present invention; and d) detecting and comparing the difference of expression of PTN in said sample cells with the non-cancerous cells.

The present invention also provides for a diagnostic kit comprising anti-PTN antibodies. Such a diagnostic kit further comprises a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

Though the antibodies of the present invention are primarily concerned with the treatment of human subjects, they may also be employed for the treatment of other mammalian subjects such as dogs and cats for veterinary purposes.

The following examples are offered by way of illustration and not by way of limitation. The disclosures of all citations in the specification are expressly incorporated herein by reference in their entirety.

EXAMPLES

Example 1

Expression of PTN and PTN Fusion Proteins

Figure 3:
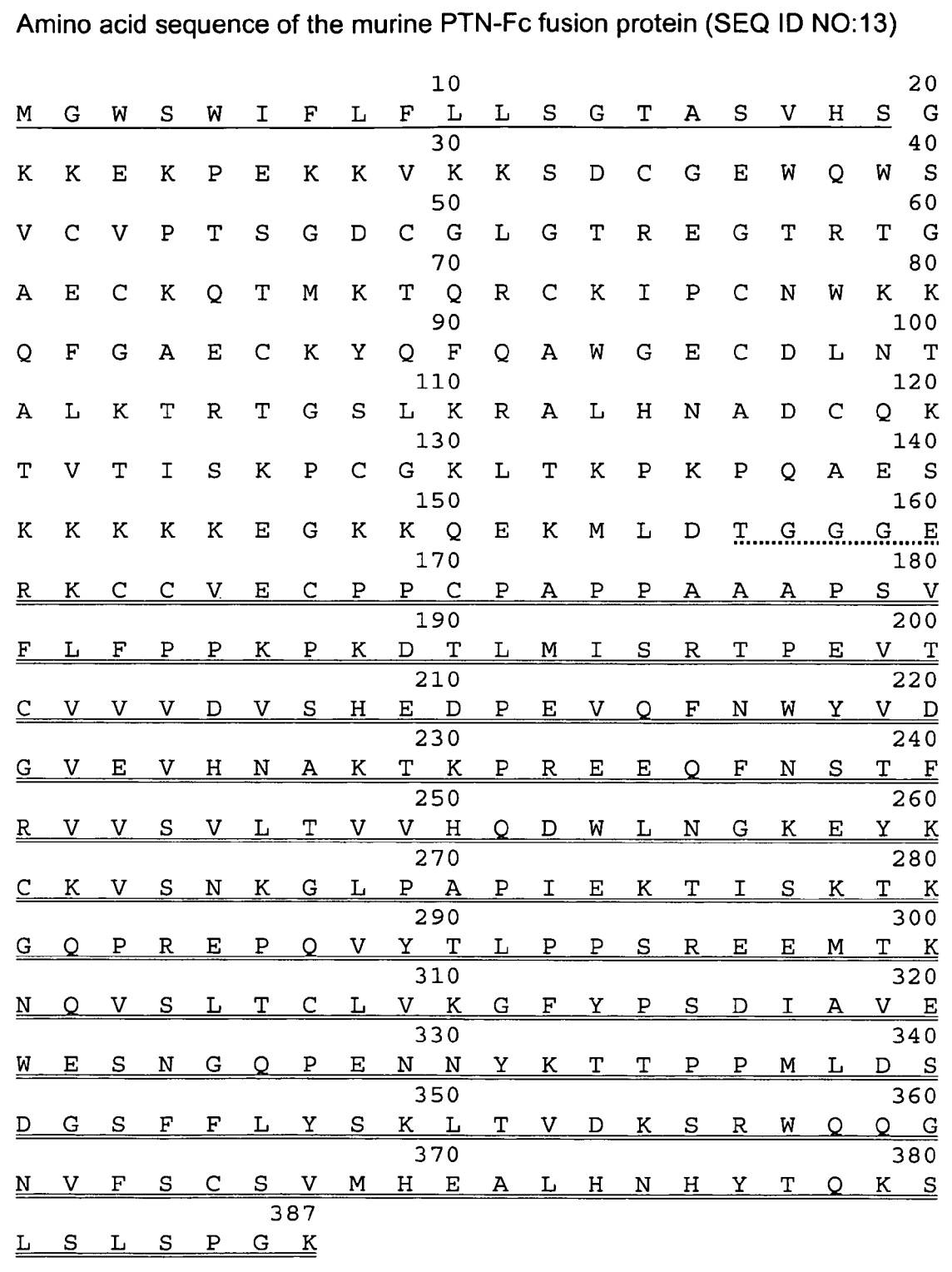
Figure 4:
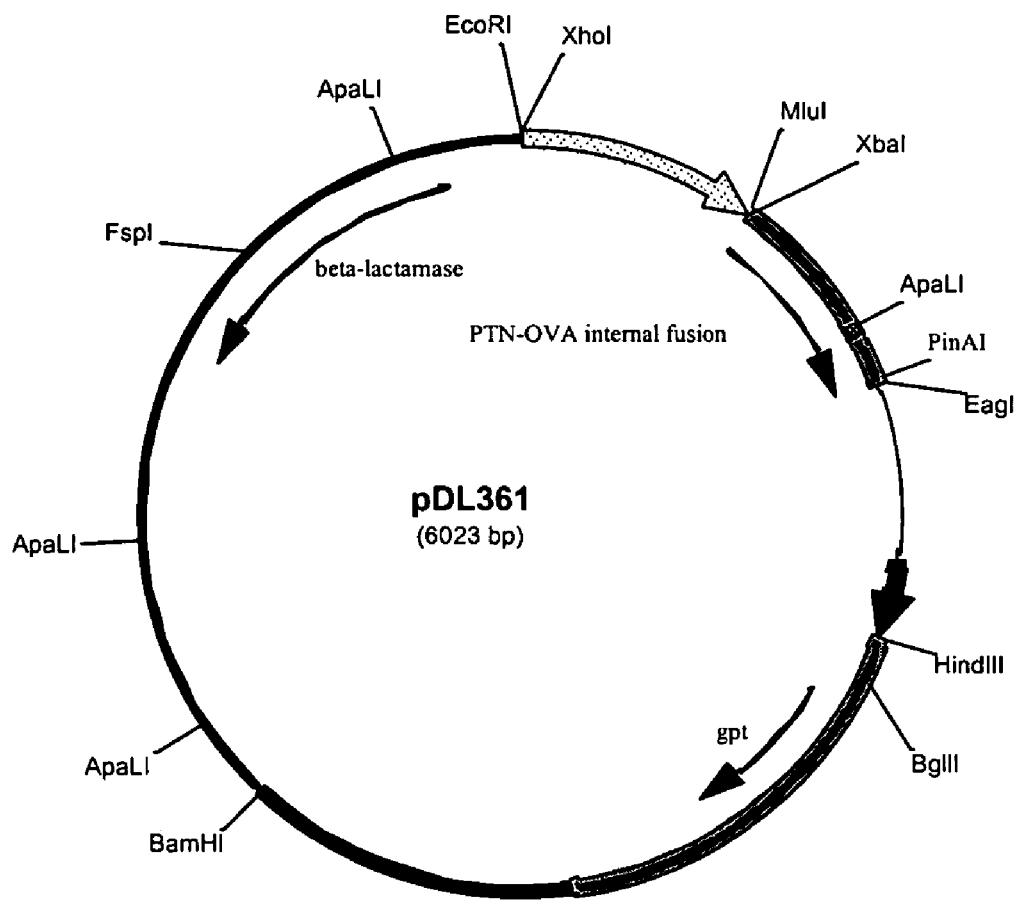
FIG. 4. The plasmid map of pDL361 for the expression of the PTN-OVA construct.
Figure 5:
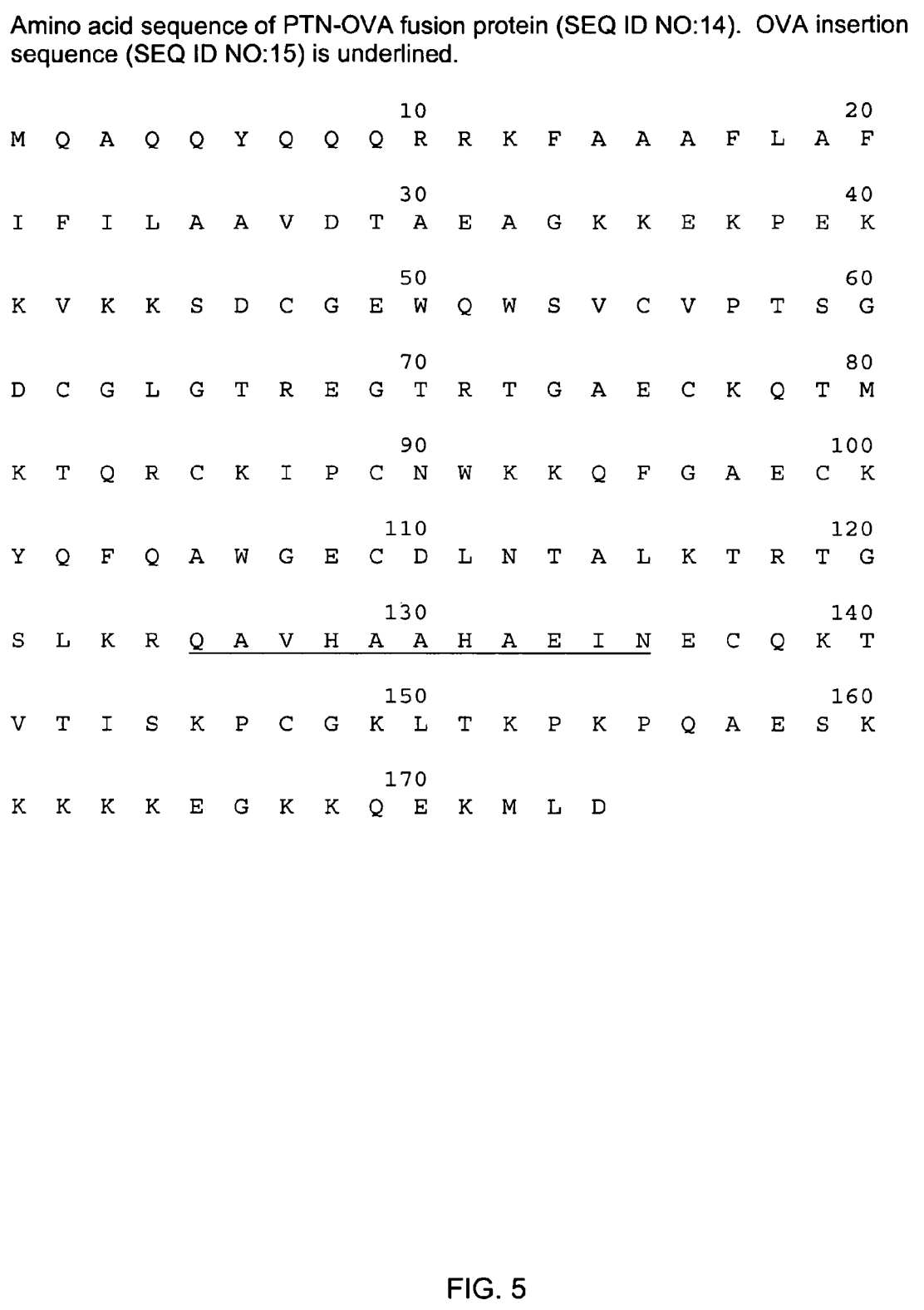

PTN cDNA was cloned into an expression vector and transfected into human adrenal gland cancer cell line SW13 to generate a stable transfectant SW13/PTN (W28, Anton Wellstein, Lambardi Cancer Center, Washington D.C., see Wellstein et. al. J. Biol. Chem. 267: 2582, (1992)). PTN-Fc fusion protein was expressed by transfecting the expression vector pDL343 (murine PTN-Fc (mPTN-Fc), see FIGS. 2 and 3) or pDL342 (human PTN-Fc (hPTN-Fc)) into myeloma cell line NS0 to generate stable production cell lines. PTN-OVA fusion protein was expressed similarly using the expression vector pDL361 (see FIGS. 4 and 5) in NS0.

Purification of PTN

Recombinant human PTN was obtained from R & D Systems, Minneapolis, Minn. (cat# 252-PL). The protein was transfected into SW13 cells, and expressed and purified from SW13 transfectants. The purified protein was shown to be active in proliferation, tube formation and colony formation (see below). SW13/PTN cells were cultured in IMDM (cat # 12-722F, Biowhittaker) supplemented with 2% FBS in roller bottles for 4-5 days. Two liters of supernatant was filtered via 0.2 µM filters and loaded onto a Heparin Sepharose column (cat # H-0532, Sigma Chemicals, St. Louis, Minn.) pre-equilibrated with 20 mM Hepes, pH 7.5, in a cold room temperature. The column was then washed with 100 ml of the same buffer. Active PTN fractions were eluted with 20 mM Hepes, 1M NaCl at pH 7.5. Protease inhibitors (cat # 539131, Calbiochem, San Diego, Calif.) were added to the fractions immediately after elution. For more purified PTN fractions, the elute from heparin-sepharose column was diluted with 20 mM Hepes and loaded onto the anti-PTN Mab column (AL13, PDL), which was pre-equilibrated in PBS. The column was then washed with 50 ml of PBS. Pure PTN fractions were eluted from the antibody column using 0.1 M Glycine, 0.1 M NaCl at pH 3.0. Fifty µl of 1M Tris-HCl, pH 8.0 was added to each ml of fraction to neutralize. All fractions were aliquoted on ice and stored at −80° C. For each batch of purification, a small aliquote of fractions was run on SDS-PAGE gel and visualized with the SilverXpress silver staining kit (cat# LC6100, Invitrogen, Carlsbad, Calif.) to confirm the presence of protein.

PTN and PTN-OVA fractions used for immunization were purified using similar protocol from supernatant of NS0/hPTN or NS0/hPTN-OVA cells. PTN-OVA protein was made by replacing human PTN amino acid 125-129 (ALHNA) with an OVA peptide 325-333 (QAVHAAHAEIN) (SEQ ID NO: 5) derived from chicken ovalbumin that is recognized by H-$2^d$ mice (Sette et al., Nature 328: 395-399 (1997)). Expression plasmid was transfected into mouse myeloma NS0 cells and secretion of PTN-OVA fusion protein was confirmed using ELISA and Western blot analysis.

Immunization

We purchased female BALB/c (cat # 000651), NOD/LtJ (cat # 0001976), B6. MRL-Tnfrsf6lpr (cat # 000482), and NZB/W F1/J (cat# 100008) mice from Jackson Laboratory, Bar Harbor, Me. at 4 to 5 weeks of age.

NOD/LtJ mice have a diabetes-like symptom. Diabetes in NOD/LtJ mice is characterized by insulitis, a leukocytic infiltrate of the pancreatic islets. Diabetic mice are hypoinsulinemic and hyperglucagonemic, indicating a selective destruction of pancreatic islet beta cells. Susceptibility to IDDM in NOD/LtJ mice is polygenic, and environment, including housing conditions, health status, and diet, exerts a strong effect on penetrance. NOD mice also exhibit multiple aberrant immunophenotypes including defective antigen presenting cell immunoregulatory functions, defects in the regulation of the T lymphocyte repertoire, defective NK cell function, and impaired wound healing. They also lack hemolytic complement, C5. NZBWF1/J mice develop an autoimmune disease resembling human systemic lupus erythematosus. Autoimmunity is characterized by high levels of antinuclear antibodies, hemolytic anemia, proteinuria, and progressive immune complex glomerulonephritis. The incidence and severity of with symptoms are more pronounced in females. B6. MRL-Tnfrsf6lpr mice have a mutation in the Fas pathway which is essential for apoptosis of T cells after they have been expanded under stimulation. Thus, these mice have large populations of peripheral clonal T cells in their immune system. Mice homozygous for the lymphoproliferation spontaneous mutation (Tnfrsf6lpr) show systemic autoimmunity, massive lymphadenopathy associated with proliferation of aberrant T cells, arthritis, and immune complex glomerulonephrosis.

Mice were immunized i.p. with 30 μg of fusion protein hPTN-Fc (human pleiotrophin fused with human Fc) mixed with Ribi at day 0 and 14. Serum samples from these mice were collected at day 21 to test for specific anti-PTN response. The mouse that had the best response was immunized at day 32 i.v. with 30 μg of hPTN-Fc. The spleen was harvested 4 days after the last immunization for hybridoma fusion.

To stimulate immune response with a T-cell epitope, BALB/c mice (6-week old) were immunized with either PTN protein or with PTN-OVA protein both purified from NS0 cells. For each mouse, 50 μl of purified antigen was mixed with 50 μl of Ribi adjuvant and injected i.p. at day 0 and 14. Serum samples from these mice were collected at day 21 to test for specific anti-PTN response. The mouse that had the best response was boosted at day 32 i.v. with another 50 μl of antigen. The spleen was harvested 4 days after the last immunization for fusion.

One PTN knockout mouse (Amet et al., Mol. Cell. Neuro. 17: 1014-1024, (2001)) was immunized via footpads with about 1 μg of protein (rhPTN and PTN fraction purified from SW13/PTN cells mixed 1:1) at day 0, 7, and 14. Hind leg lymph nodes from this mouse were collected at day 18 for hybridoma fusion.

Generation of Hybridomas

Single cell suspension from the spleen was made by cutting and mashing the spleen with the inside plunger of a syringe. Red blood cells were removed using RBC lysis buffer (cat# R7757, Sigma Chemicals, St. Louis, Miss.). Lymphocytes with NS0/BCL-2 cells (NS0 cells transfected with BCL-2 cDNA, PDL) were mixed and pelleted. Fusion was performed in pre-warmed 50% PEG 1500 (cat# 783641, Roche Applied Science, Indianapolis, Ind.). Cells were resuspended in HAT media [DMEM with 20% FBS, 10 mM HEPES, 50 mM β-mercaptoethanol, 1× penicillin G (10 units/ml), streptomycin (10 μg/ml), 2 mM-glutamine, 0.1 mM non-essential amino acid, 1 mM sodium pyruvate supplemented with 1×HT (cat# H-0137, Sigma Chemicals) and aminopterin (cat#A-5159, Sigma Chemicals) and Origen hybridoma cloning factor (cat#210001, IGEN International, Inc., Gaithersburg, Md.)] and plated in 96-well plates. The cells were fed once a week and screened after 14 days.

Anti-PTN ELISA

To immobilize PTN for ELISA, 96-well ELISA plates (MAXISORP NUNC cat# 439454, VWR Scientific Products, Goshen Parkway West Chester, Pa.) were coated with 100 μl of rhPTN at 0.5 μg/ml (cat# 252-PL, R&D Systems) at 4° C. overnight and blocked with 200 μl Pierce SuperBlocking Buffer in TBS (cat #37535, Pierce, Rockford, Ill.) at room temperature for 30 minutes before use. Alternatively, PTN was immobilized by capturing it from SW13/PTN supernatant using antibodies. Plates were coated with 100 μl goat anti-human PTN polyclonal antibodies (cat# AF252-PB, R&D Systems) at 1 μg/ml diluted in 0.2 M sodium bicarbonate, pH 9.4 (cat # 28382, Pierce) at 4° C. overnight. After washing, 100 μl of freshly collected filtered SW13/PTN supernatant (conditioned medium from a 4-5 day culture) was loaded per well and incubated at 4° C. for 4-5 hours. The plates were then washed and blocked as described above.

To detect binding activity of anti-PTN hybridomas, 50 μl supernatant from the hybridoma clones were added to each well and incubated at 4° C. overnight. The plates were then incubated with horseradish peroxidase-conjugated goat anti-mouse IgG Fcγ (subclass 1+2a+2b+3) specific antibodies (cat# 115-035-164, Jackson ImmunoResearch, West Grove, Pa.) at room temperature for 1 hour and detected with 100 μl/well of 1:1 diluted TMB Peroxidase Substrate (cat# 50-76-02, KPL) in Peroxidase Solution (cat# 50-65-02, KPL, Gaithersburg, Md.). The reaction was stopped with 100 μl of 2N $H_2SO_4$ and the plates were read at 450 nm with an ELISA Reader (Molecular Device, Sunnyvale, Calif.).

For cell ELISA, SW13 cells in IMDM+2% FBS+1% P/S were seeded at $0.2 \times 10^6$ cells per well onto 96-well plates and grown to 100% confluence. Plates were washed and air-dried overnight, blocked with Super Blocking Buffer in PBS (cat #3 7515, Pierce). The washed plate was then processed with the protocol as described above to detect anti-PTN activity of hybridomas.

Antibody Characterization

The isotype of each hybridoma antibody was determined by using a mouse monoclonal antibody isotyping kit (cat. # 10126-019, Invitrogen, Carlsbad, Calif.). Hybridomas were expanded in Gibco's Hybridoma-SFM (cat. # 12045-076, Invitrogen). Monoclonal antibodies were purified from hybridoma supernatant by protein-G affinity chromatography.

Amino Acid Sequencing

3B10 was sequenced both with and without deblocking of the heavy chain. For N-terminal sequencing of the light chain, 30 µg of the antibody was sequenced, without prior deblocking, by automated Edman degradation and PTH analysis on a Model 241 Protein Sequencer (Hewlett Packard, Palo Alto, Calif.). The PTH derivatives were analyzed on a Hypersil ODS C18 column. The sequencer and HPLC were operated according to the manufacturer's instructions using reagents, solvents, and columns obtained from Hewlett Packard.

For N-terminal deblocking, 3B10 antibody (30 µg) were reduced in 4.0 M guanidine-HCl, 0.1 M Tris-HCl (pH 8.5), 0.0005 M EDTA, and 0.02 M-0.07 M DTT for 15 minutes at 90° C. under argon, carboxymethylated by addition of iodoacetic acid to 0.06 M-0.2 M for 60 minutes at 37° C. in the dark, cooled at room temperature for 15 minutes, and immediately buffer-exchanged in 0.1 M sodium phosphate (pH 7.5), 0.002 M EDTA using a NAP5 column (Cat. # 17-0853-02, Amersham Pharmacia Biotech, Arlington Heights, Ill.). The eluate was adjusted to 0.012 M DTT, 5% glycerol. The sample was then digested with 4000 µU of pyroglutamate aminopeptidase (Cat. # 7334, Takara Shuzo Co., Ltd., Tokyo, Japan) for 24 hours at 50° C. For determination of the light chain and heavy chain sequences, the entire deblocked sample was sequenced as described above.

Determination of Antibody Variable Region Sequences

Total RNA was extracted from approximately $10^7$ hybridoma cells using TRIzol reagent (Life Technologies, Gaithersburg, Md.) and poly(A)$^+$ RNA was isolated with the PolyATract mRNA Isolation System (Promega, Madison, Wis.) according to the suppliers' protocols. Double-stranded cDNA was synthesized using the SMART™RACE cDNA Amplification Kit (Clontech, Palo Alto, Calif.) following the supplier's protocol. The variable region cDNAs for the light and heavy chains were amplified by polymerase chain reaction (PCR) using 3' primers that anneal respectively to the mouse kappa and gamma chain constant regions, and a 5' universal primer provided in the SMART™RACE cDNA Amplification Kit. The 5' universal primer for VL has the sequence: 5' GAT GGA TAC AGT TGG TGC AGC-3' (SEQ ID NO:16) and for VH has the sequence: 5'-GCC AGT GGA TAG ACA GAT GG-3' (SEQ ID NO: 17).

For VL PCR, the 3' primer has the sequence: 5'-TATA-GAGCTCAAGCTTGGATGGTGGGAAGATG-GATACAGTTGGTGC-3' (SEQ ID NO:18) with residues 17-46 hybridizing to the mouse Ck region. For VH PCR, the 3' primers have the degenerate sequences: 5'-TATAGAGCT-CAAGCTTCCAGTGGATAGAC(ACT)GATGGGG(GC) TGT(CT) GTTTTGGC-3' (SEQ ID NO: 19) with residues 17-50 hybridizing to mouse gamma chain CH1. The VL and VH cDNAs were subcloned into pCR4Blunt-TOPO vector (Invitrogen, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions. The sequencing reactions were analyzed on a Model 377 DNA Sequencer (Applied Biosystems).

Proliferation Assay

Five thousand tissue culture cells were seeded per well in 96-well plates in full media and incubated at 37° C. overnight. Filter-sterilized PTN fractions purified from SW13/PTN cells were added to the cells with antibodies (1 µg/ml). After 48 hours of incubation, cell proliferation was quantitated by using Alamar Blue (cat# DAL1100, BioSource) according to the manufacturer's protocol and read in a fluorescence plate reader (SPECTRA Max GeminiXS, Molecular Device).

Soft Agar Assay

SW13 (human adrenal carcinoma) cells were seeded on a layer of bottom agar as single-cell suspension in 0.35% agar (cat# 50100, BMA) in IMDM supplemented with 10% FBS. Colonies were stained with crystal violet and counted under the microscope after 2-3 weeks.

Tube Formation Assay

Two hundred and fifty µl of Matrigel (cat# 356235, Becton Dickinson, Franklin Lakes, N.J.) was plated per well in 24-well plates and incubated at 37° C. for 30 min. HUVEC cells (cat # CC-2519, Clonetics, San Diego, Calif.) were trypsinized and resuspended in EBM-2/1% FBS (cat # CC-3156, Clonetics). For each well, 25,000 cells and 125 µl of supernatant from SW13/PTN cells were plated on top of matrigel with anti-PTN antibodies (5 µg/ml). Each antibody assay was done in duplicate wells. After 17-20 hours of incubation, number of tubes for each well was counted under light microscope manually. In addition, live cells were labeled with Calcium-AM (cat# C-3100, Molecular Probe, Eugene, Oreg.) in PBS. Picture for each well was taken under the fluorescence microscope and quantitated using a Discovery-1 software (Universal Imaging Corporation, Downington, Pa.).

Animal Study

Each six week-old female ICR scid mouse (cat# ICRSC-M, Taconics) was inoculated subcutaneously in the mid-scapular region with 5 million human tumor cells in cold sterile PBS. For prevention models, the animals were treated with 200 µg of antibody i.p., 3 times a week starting the day after tumor cell injection. For future treatment models, animals will be randomized into different groups when the tumor volume reaches 100 mm$^3$. The animals will then be treated with 200 µg of antibodies every day i.p. The tumors will be measured every 2-3 day as length×width×height.

Results: Generation of Anti-PTN Antibodies

Pleiotrophin (PTN) is highly conserved among different species. There is only one amino acid difference between mouse and human PTN (FIG. 1); and thus it is difficult to generate antibodies for PTN. We first made a fusion protein of PTN fused with human Fc IgG2M3 (Cole et al., J. Immunol. 159: 3613-3621 (1997)) in NS0 cells and purified the protein using protein A affinity column. BALB/c mice were immunized with the murine PTN-Fc fusion protein in the footpad and boosted twice. Lymph nodes from these mice were harvested and fused with NS0 myeloma cells. Five anti-PTN antibodies were generated from this method of immunization using 2 BALB/c mice (See Table 1). None was functional in blocking the action of PTN. One of them, AL13, was later used to make anti-PTN affinity column to purify PTN.

TABLE 1

Summary of fusions from different immunizations.

| Mouse Strain | Immunogen | Number of PTN positive hybridomas | Number of mice used |
|---|---|---|---|
| Balb/C | mPTN-Fc | 5 | 2 |
| lpr/lpr | hPTN-Fc | 11 | 4 |
| NZB/W F1 | hPTN-Fc | 4 | 1 |
| Balb/C | PTN-OVA | 20 | 1 |
| PTN KO | rhPTN/PTN frac. | 99 | 2 |

Next we used different strains of autoimmune mice to take advantage of their dysfunctional immune system to generate autoantibodies. We selected NOD, lpr/lpr and NZB/F1 mice because they have defects in different components of the immune system. Four week-old female mice were immunized i.p. with 30 µg of human PTN-Fc at day 0 and day 14.

Figure 6:
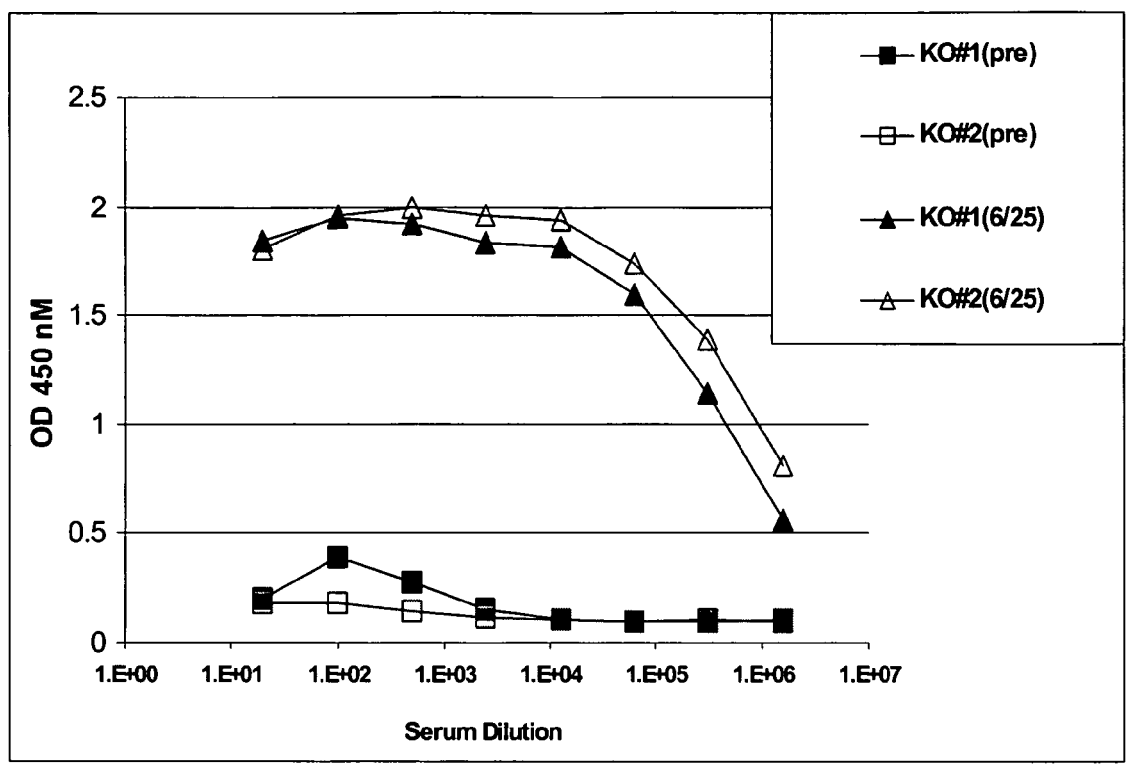
FIG. 6. Serum Titer of anti-PTN antibodies in immunized mice. A. Different strains of female mice (6 week-old) were immunized i.p. with 30 µg of hPTN-Fc at day 0 and day 14. Serum samples from these mice were collected to test for specific anti-PTN response. B. BALB/c mice (6-week old) were immunized with either PTN protein (indicated by squares) or PTN-OVA protein (indicated by triangles). For each mouse, 50 µl of purified antigen was mixed with 50 µl of Ribi adjuvant and injected i.p. at day 0 and 14. Serum samples from these mice were collected at day 21 to test for specific anti-PTN response. C. PTN KO mice were immunized via footpad with rhPTN and PTN fraction purified from SW13/PTN supernatant at day 0 and 14. Serum samples from these mice were collected before (Pre) and after (6/25) the immunization to test for specific anti-PTN response.

Serum samples from these mice were collected to test for specific anti-PTN response. As shown in FIG. 6A, almost all the autoimmune mice had better response to PTN than the BALB/c mice. We picked several mice with good response and boosted them one more time with human PTN-Fc and performed hybridoma fusions using their spleens. Many antibodies were of IgM isotype. Two anti-PTN antibodies of the IgG isotype were obtained in these fusions.

In order to have a bigger repertoire of anti-PTN antibodies, we decided to recruit additional T cell help in our immunization protocol by using a PTN immunogen containing a T-cell epitope. Human PTN molecules with or without the OVA peptide (T cell epitope that reacts with H-2d mice, see Sette et al., Nature 328: 395-399 (1997)) were expressed in NS0 cells and purified by affinity chromatography. In order to demonstrate the stimulatory effect of a T-cell epitope, BALB/c mice were immunized with PTN or PTN-OVA. We collected serum samples from these mice and tested their immune response to PTN by ELISA (FIG. 6B). Mice immunized with PTN-OVA protein clearly showed enhanced anti-PTN response compare to mice immunized with PTN protein without OVA peptide insertion. The serum titers of the PTN-OVA immunized mice were at least 640-fold higher than those of the PTN immunized mice. These mice were then used to generate hybridomas against PTN.

To get even a bigger repertoire of anti-PTN antibodies, we immunized PTN-knockout mice (see Amet et al., Mol. Cell. Neuro. 17: 1014-1024 (2001)) with purified PTN mixed with recombinant human PTN. The rationale is that, since these mice never expressed PTN as a self-protein, the immune response should be excellent against PTN. The data showed in FIG. 6C support this hypothesis. Comparing the anti-PTN titers of the pre-immune and post-immune sera of the two PTN-knockout mice, a rigorous immune response to PTN was demonstrated. The anti-PTN titers in these mice were at least 100-1000 fold higher than those in PTN-OVA immunized mice.

Figure 7:
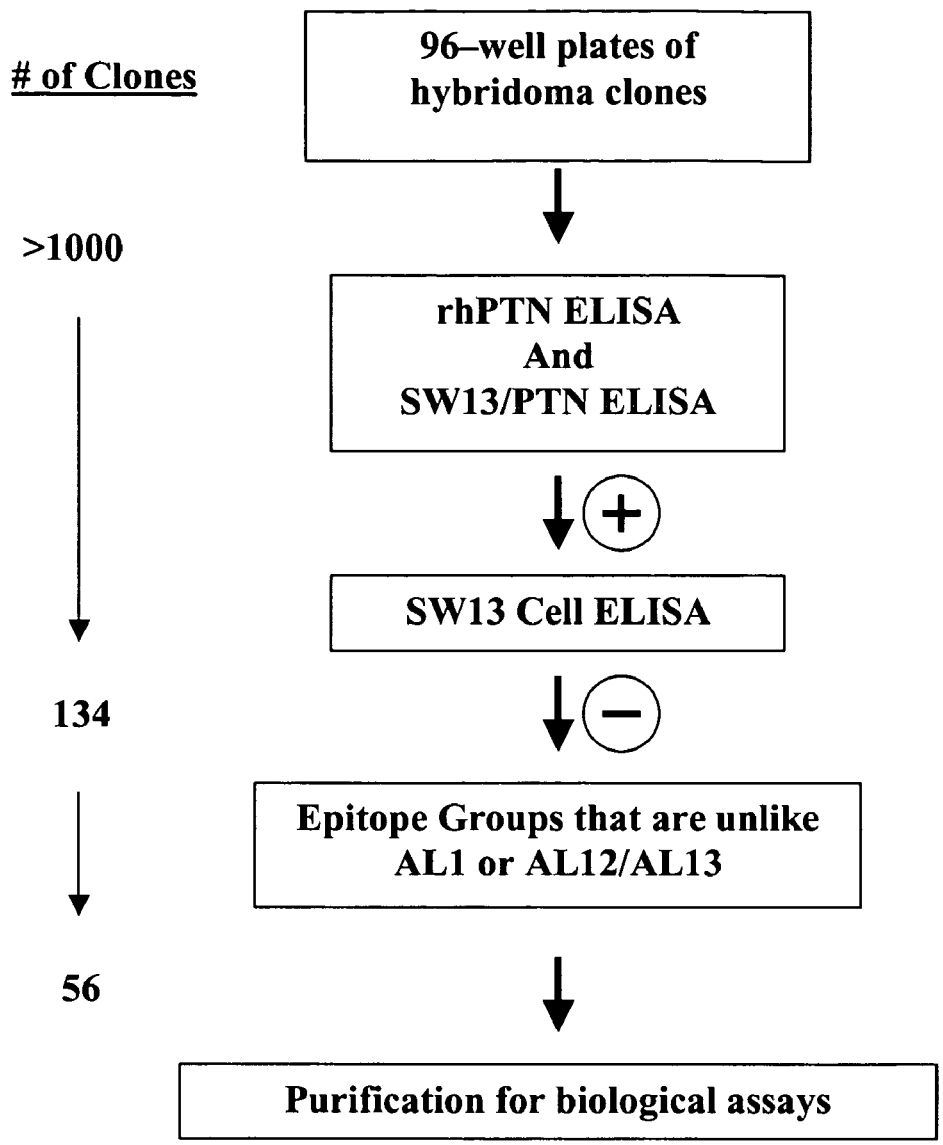
FIG. 7. Flow chart of screening strategies for PTN-specific hybridomas. All hybridoma clones were screened using multiple ELISA assays as shown. Hybridoma clones that bind to recombinant human PTN (rhPTN) and SW13/PTN supernatant, but not SW13 cells were chosen for expansion. The hybridoma clones were then epitope mapped against biotynilated AL1 or AL12. Only clones that react to epitopes different from either group were expanded for biological assays.

From the PTN-OVA immunized BALB/c mice or PTN immunized PTN knockout mice, we picked animals that had the best response to perform hybridoma fusions. To identify hybridoma clones that react specifically with PTN, we selected clones that make antibodies that bind not only to the inactive recombinant human PTN (rhPTN) but also to functional PTN secreted by mammalian cells (SW13/PTN). In addition, we screened all these clones with a SW13 cell plate assay to eliminate those that bind to SW13 cellular components other than PTN (see flow chart in FIG. 7). Hybridoma clones that were specific for PTN were then chosen for further characterizations.

Table 1 summarized the number of PTN-specific antibodies generated from different immunization schemes. As expected, the PTN knockout method was the best, giving 99 anti-PTN hybridomas from two mice. The PTN-OVA method gave 20 PTN-specific hybridomas from one animal. Using autoimmune animals to make anti-PTN also appears to be good. The T-cell epitope tagging method gave us many good anti-PTN hybridomas that were not possible with the conventional method. It should be the method of choice to break tolerance when knockout mice for certain genes are not available.

As mentioned above, we had generated 5 anti-PTN antibodies (the AL series) from two BALB/c mice that were immunized with mPTN-Fc. Although some of the antibodies have high affinity toward PTN, none of them were functional. We epitope mapped these 5 antibodies and found that they can be separated into two distinct groups, AL1 or AL12/AL13. Thus, we screened all newly generated PTN-specific hybridoma clones against biotinylated AL1 or AL12 to find those clones that are reactive to different epitopes of PTN. As we expected, most of PTN-specific hybridomas generated from autoimmune mice still belong to either AL1 or AL12/AL13 epitope groups. However, about half of hybridoma clones from PTN-OVA immunized BALB/c mouse or PTN immunized PTN-deficient mice belong to new epitope groups (see FIG. 7). We reasoned that these clones should have the better potential to be neutralizing antibodies than the AL series, therefore we expanded these hybridoma clones for small scale purifications and tested their antibody functions in biological assays.

Results: Amino Acid and DNA Sequence of the Anti-PTN Antibodies

The NH2-terminal sequence of 3B10 was first determined. When 3B10 was subjected to Edman degradation, only one sequence corresponding the light chain was obtained, indicating the heavy chain is blocked, most likely due to the modification of the NH2-terminal glutamine residue. The first 16 amino acid residues of the 3B10 were determined to be: DIVMTQSPSLAMSVG (SEQ ID NO: 20). With deblocking, two residues were released for each cycle of Edman degradation. After subtracting the light chain sequence, the first 17 amino acid residues of 3B10 were determined to be: QVQLQQSGPELVKPGAS (SEQ ID NO: 21).

The amino acid and the DNA sequences of the entire VH of 3B10 and VL were then determined and the sequences were shown in FIGS. 1B and 1C, respectively. The amino terminal residues of derived mature VH and VL sequences correspond exactly those determined by amino acid sequencing, confirming the correct VH and VL of 3B10 was cloned.

Figure 8:
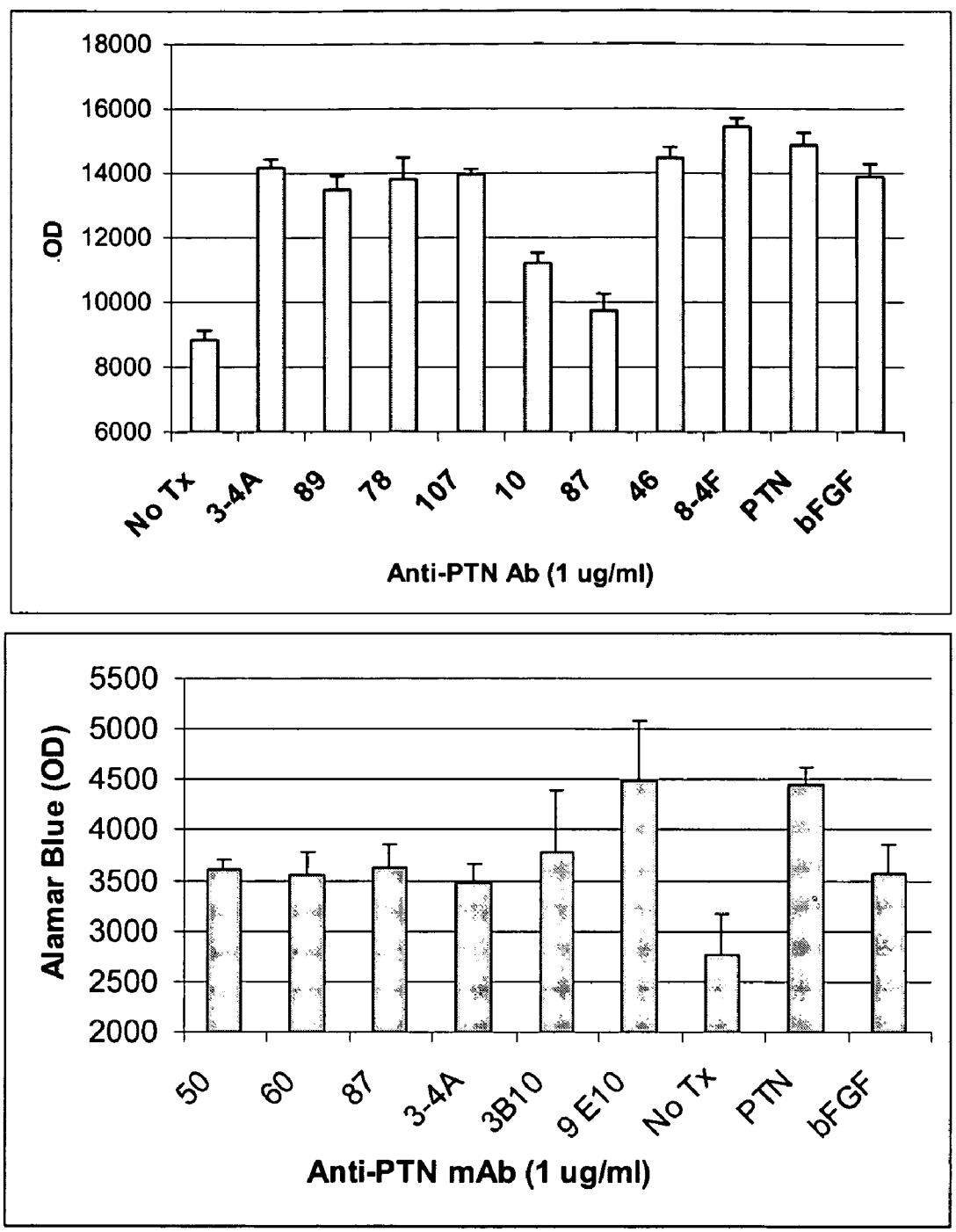
FIG. 8. Anti-PTN antibodies inhibit cell proliferation. Five thousand U87MG cells (A) or NIH3T3 cells (B) per well were seeded in 96-well plates and incubate at 37° C. O/N. Purified PTN fractions were added to the cells with antibodies (1 µg/ml) in media with 0.4% FBS. After 48 hours of incubation, cells were quantitated using Alamar Blue assay. "No Tx" represents wells without any growth factor stimulation. "PTN" sample indicates wells without antibody treatment. bFGF at 1 ng/ml was used as positive control. 9E10 is a non-specific control antibody.

Results: Inhibition of Cell Proliferation, Anchorage Independent Growth and in Vitro Angiogenesis by Anti-PTN Antibodies In order to identify antibodies that can neutralize the mitogenic activity of PTN, we tested our panel of antibodies in cell proliferation assays. In FIG. 8A, human glioblastoma U87MG cells were stimulated with PTN for growth. Several anti-PTN antibodies could inhibit the cell proliferation by PTN from 10-80%. We tested the antibodies in several different cell lines that are dependent on PTN for growth. Another example is shown in FIG. 8B mouse NIH3T3 cell proliferation was also inhibited with different anti-PTN antibodies ranging from 10 to 77%. The data demonstrated that our anti-PTN antibodies not only bound to PTN, but also functionally blocked the mitogenic activity of PTN.

Figure 9:
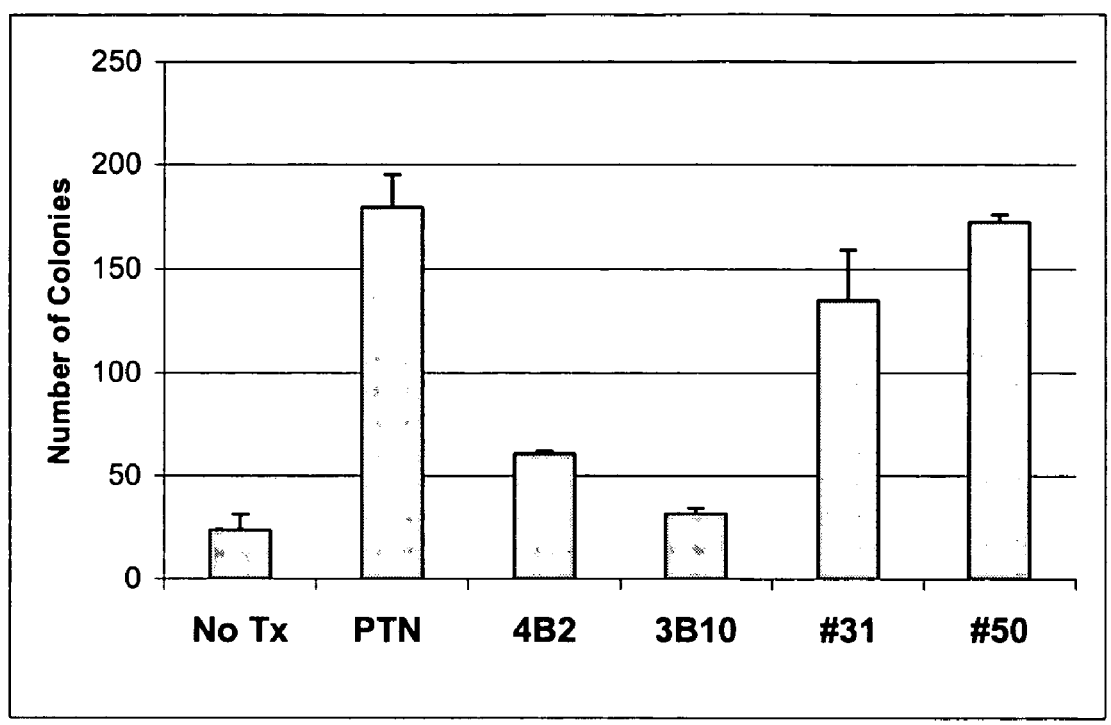
FIG. 9. Anti-PTN antibodies inhibit colony formation in soft agar. SW13 cells do not form many colonies in soft agar without any growth factor (No Tx). Cells were plated in soft agar with the stimulation of pleiotrophin (PTN). At the same time, different anti-PTN monoclonal antibodies (10 µg/ml) were added to the mixture. Colonies were counted after 14 days in culture. Each antibody was done in duplicate wells for every experiment. 4B2 and 3B10 mAbs inhibit soft agar formations up to 95% in 3 separate experiments.

Anchorage independent growth of tumor cells in vitro has been shown to have the best correlation in predicting tumorigenicity in vivo. Human adrenal carcinoma SW13 cells do not form many colonies in soft agar without additional growth factor. Addition of PTN to these cells stimulates their anchorage independent growth of colonies in soft agar. Subsequently, we tested all the potential neutralizing anti-PTN antibodies in a soft agar colony formation assay. As shown in FIG. 9, several anti-PTN antibodies that we have generated can inhibit colony formation in soft agar up to 95%. These data show that we are able to generate antibodies that can neutralize the oncogenic activity of PTN in vitro.

Lastly, we tested whether anti-PTN antibodies can inhibit angiogenesis. Human endothelial cells (HUVEC) form tube-like structures when they are stimulated with angiogenic factors and plated on Matrigel®. Supernatant from SW13/PTN cells stimulated tube formation of HUVEC cells (FIG. 10), but such a formation was inhibited by some anti-PTN antibodies (see the representative antibody #27, FIG. 10). These experimental results indicated that some of our anti-PTN antibodies also inhibited in vitro angiogenesis induced by PTN.

Taken together, these experiments demonstrated that we are able to generate a panel of anti-PTN antibodies that have neutralizing activity against PTN functions. A summary of these antibodies and their inhibitory functions in different assays is shown in Table 2. Interestingly, not all of our antibodies have the same neutralizing activities against PTN. Most of them inhibited either the soft agar colony formation assay or the tube formation assay. However, a few of them did inhibit both oncogenic and angiogenic activities of PTN. Clones that show inhibitory activities were then sub-cloned and expanded again to produce large amount of antibodies for in vivo studies.

TABLE 2

Summary of potential neutralizing anti-PTN antibodies.
Candidates for neutralizing antibodies

| Clone | | ELISA | | Proliferation | | | Tube | Soft |
|---|---|---|---|---|---|---|---|---|
| ID | Mouse | rhPTN | SW13/PTN | NIH 3T3 | U87 MG | WI38 | Assay | Agar |
| 3B10 | NZB #1 | 0.597 | 0.139 | ++ | ++ | + | − | ++++ |
| 4B2 | NZB #1 | 2.17 | 0.222 | + | ++ | − | − | +++ |
| 10 | PTN KO | 0.65 | 0.40 | +++ | +++ | + | ND | +/− |
| 17 | PTN KO | 0.75 | 0.11 | + | + | | − | +/− |
| 24 | PTN KO | 0.64 | 0.19 | + | + | +/− | − | ++ |
| 25 | PTN KO | 0.85 | 0.45 | ++ | ++ | ++ | ++ | − |
| 26 | PTN KO | 0.75 | 0.32 | + | + | +/− | − | − |
| 27 | PTN KO | 0.85 | 0.15 | ++ | ++ | ++ | ++ | +/− |
| 31 | PTN KO | 0.95 | 0.71 | ++ | − | + | + | + |
| 41 | PTN KO | 1.06 | 0.40 | + | + | − | − | +/− |
| 50 | PTN KO | 0.99 | 0.53 | ++ | ++ | + | +/− | +/− |
| 60 | PTN KO | 0.85 | 0.44 | + | + | − | ND | +/− |
| 87 | PTN KO | 0.93 | 0.21 | ++ | ++ | + | +/− | ++ |
| 3-4A | Balb/c #2 | 1.00 | 0.58 | ++ | ++ | − | ND | +/− |

In Table 2, the column title "mouse" indicates where the hybridoma clone came from. ELISA values (in OD unit) indicate their binding affinities. The rest of columns show the results of multiple functional assays. 'ND' indicates not done. '−' shows that the antibody has no affect on the assay. "+" is about 25% inhibition. "++" represents 50% inhibition. "+++" represents 75% inhibition. "++++" represents complete inhibition.

Results: Anti-PTN Antibody Suppresses Human Tumor Growth and Metastasis in Vivo

Figure 11:
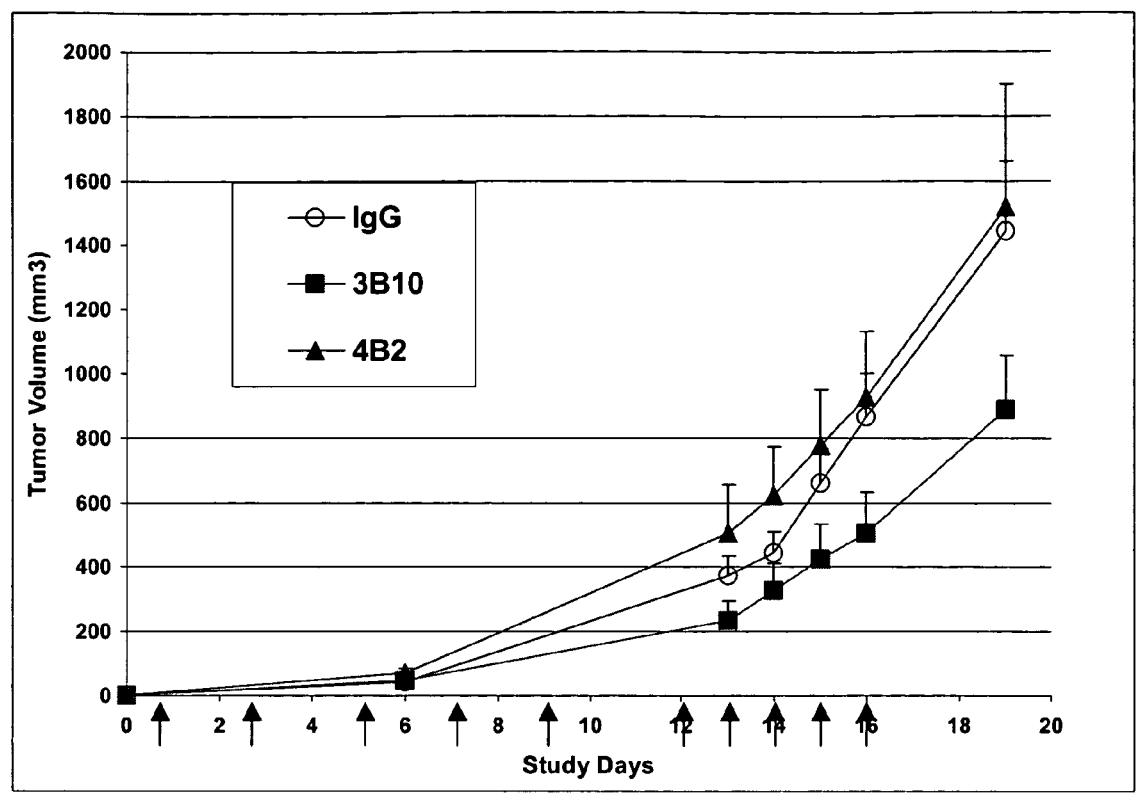
FIG. 11. Anti-PTN antibodies suppress human pancreatic tumor growth in vivo. Six week-old female ICR SCID mice (Taconics) were each inoculated with 5 million COLO357 cells. Starting the day after cell injection, the animals were treated with 200 µg of antibody i.p. Solid arrows indicate the days for antibody treatments. The tumors were measured every 2-3 day as length×width×height. Each group includes 9 mice.

A xenograft model was used to test the efficacy of the anti-PTN antibodies in vivo of the most potent antibodies that are inhibitory to the PTN-mediated colony formation, 3B10 and 4B2 in Table 2, were picked to test in a pancreatic cancer model using human pancreatic tumor COLO357 cells. These cells were inoculated subcutaneously into immuno-deficient scio mice and the animals were treated with anti-PTN antibodies to prevent tumor growth. As shown in FIG. 11, one of the two anti-PTN antibodies tested, 3B10, suppressed the tumor growth about 40% compared to the control IgG antibodies or 4B2.

The efficacy of the anti-PTN antibodies in treating established tumors are also tested using this xenograft model. For solid tumor models, such as COLO357 (pancreatic cancer), U87MG (glioblastoma), JEG-3 (choriocarcinoma), or MDA-MB-231 (breast) xenograft, six to eight week old female scid mice are inoculated subcutaneously in the mid-scapular region with 2 to 5 million cells. Anti-PTN antibodies are given intraperitoneally when tumors reach an average size of 100 mm$^3$, three to seven times per week for 3-4 weeks. The tumors are measured every 2-3 day as length×width×height with vernier calipers.

Example 2

Efficacy of Anti-PTN Antibodies in Additional Tumor Models

The efficacy of the anti-PTN antibodies in treating tumor metastasis may also be examined using xenograft models. For a melanoma metastasis model, such as 1205LU xenograft, six to eight week old female scid mice are inoculated subcutaneously in the mid-scapular region with 1×10$^6$ cells. Anti-PTN antibodies are given intraperitoneally when tumors reach an average size of 100 mm$^3$, three times per week for 3-4 weeks. The tumors were measured every 2-3 day as length×width×height with vernier calipers. The lung metastases are monitored at the end of the experiment by sacrificing the animals and dissecting their lungs. Paraffin embedding and histology sections of lungs will be used to check for micrometastases.

Similarly, COLO357 pancreatic cells may be used for a liver metastasis model. Six to eight week old female SCID mice are inoculated with 5×10$^6$ cells intraperitoneally. Anti-PTN antibodies are given intraperitoneally 5 to 7 days after injection of tumor cells, daily for 2-3 weeks. The metastases are monitored at the end of the experiment by sacrificing the animals and dissecting their livers. Paraffin embedding and histology sections of livers will be used to check for micrometastases.

Although the invention has been described with reference to the presently preferred embodiments, it should be understood that various modifications may be made without departing from the spirit of the invention.

All publications, patents, patent applications, and web sites are herein incorporated by reference in their entirety to the same extent as if each individual patent, patent application, or web site was specifically and individually indicated to be incorporated by reference in its entirety.

We claim:

1. An isolated antibody or antigen-binding fragment thereof that specifically binds to pleiotrophin (PTN) comprising any one of the following:
   (a) a monoclonal antibody or antigen-binding fragment thereof produced by hybridoma cell line 3B10 having ATCC deposit designation PTA-11180;
   (b) an antibody or antigen-binding fragment thereof that binds to an epitope, which is the same as an epitope of the monoclonal antibody or antigen-binding fragment thereof produced by hybridoma cell line 3B10 having ATCC deposit designation PTA-11180; or
   (c) an antibody that competitively inhibits binding of a PTN polypeptide to an antibody comprising: (i) a light chain CDR1 sequence of SEQ ID NO:10, (ii) a light chain CDR2 sequence of SEQ ID NO:11, (iii) a light chain CDR3 sequence of SEQ ID NO:12, (iv) a heavy chain CDR1 sequence of SEQ ID NO:5, (v) a heavy chain CDR2 sequence of SEQ ID NO:6 and (vi) a heavy chain CDR3 sequence of SEQ ID NO:7.

2. The antibody or antigen-binding fragment thereof according to claim 1, wherein the antibody or antigen-binding fragment comprises: (i) a light chain CDR1 sequence of SEQ ID NO:10, (ii) a light chain CDR2 sequence of SEQ ID NO:11, (iii) a light chain CDR3 sequence of SEQ ID NO:12, (iv) a heavy chain CDR1 sequence of SEQ ID NO:5, (v) a heavy chain CDR2 sequence of SEQ ID NO:6 and (vi) a heavy chain CDR3 sequence of SEQ ID NO:7.

3. The antibody or antigen-binding fragment thereof according to claim 2, wherein said antibody comprises a heavy chain variable domain amino acid sequence comprising SEQ ID NOs: 3 and a light chain variable domain amino acid sequence comprising SEQ ID NOs: 8.

4. The antibody or antigen-binding fragment thereof according to claim 1, wherein said antibody is selected from the group consisting of a chimeric antibody, humanized antibody, and a fully human antibody.

5. The antibody or antigen-binding fragment thereof according to claim 1, wherein said antigen-binding fragment is selected from the group consisting of Fab fragment, (Fab')$_2$ Fragment, and a Fv fragment.

6. The antibody or antigen-binding fragment thereof of claim 1, wherein the antibody is conjugated to a cytotoxic agent.

7. The antibody or antigen-binding fragment thereof according to claim 1, wherein said antibody binds to a PTN epitope at a binding affinity of at least $10^6 M^{-1}$.

8. A pharmaceutical composition comprising the antibody according to claim 1 and a pharmaceutical carrier.

* * * * *

UNITED STATES PATENT AND TRADEMARK OFFICE
CERTIFICATE OF CORRECTION

| | | |
|---|---|---|
| PATENT NO. | : 7,888,485 B2 | |
| APPLICATION NO. | : 10/812366 | |
| DATED | : February 15, 2011 | |
| INVENTOR(S) | : Tso et al. | |

It is certified that error appears in the above-identified patent and that said Letters Patent is hereby corrected as shown below:

In claim 3, column 42, line 7 please replace "SEQ ID NOs:" with --SEQ ID NO:--

In claim 3, column 42, line 8 please replace "SEQ ID NOs:" with --SEQ ID NO:--

Signed and Sealed this
Twelfth Day of April, 2011

David J. Kappos
*Director of the United States Patent and Trademark Office*